(12) United States Patent
Casseday et al.

(10) Patent No.: US 10,653,660 B2
(45) Date of Patent: *May 19, 2020

(54) METHODS OF IMPROVING THE PHARMACOKINETICS OF DOXEPIN

(71) Applicant: Pernix Sleep, Inc., Morristown, NJ (US)

(72) Inventors: Cara Baron Casseday, San Diego, CA (US); Elizabeth Ludington, San Diego, CA (US); Michael Skinner, San Diego, CA (US); Susan E. Dubé, Carlsbad, CA (US); Roberta L. Rogowski, Rancho Santa Fe, CA (US); Philip Jochelson, San Diego, CA (US); Robert Mansbach, San Diego, CA (US)

(73) Assignee: Currax Pharmaceuticals LLC, Morristown, NJ (US)

( * ) Notice: Subject to any disclaimer, the term of this patent is extended or adjusted under 35 U.S.C. 154(b) by 0 days.

This patent is subject to a terminal disclaimer.

(21) Appl. No.: 15/436,293

(22) Filed: Feb. 17, 2017

(65) Prior Publication Data

US 2017/0157140 A1   Jun. 8, 2017

Related U.S. Application Data

(63) Continuation of application No. 13/653,213, filed on Oct. 16, 2012, now Pat. No. 9,572,814, which is a continuation of application No. 13/007,334, filed on Jan. 14, 2011, now abandoned, which is a continuation of application No. 11/781,165, filed on Jul. 20, 2007, now Pat. No. 7,915,307.

(60) Provisional application No. 60/833,617, filed on Jul. 24, 2006, provisional application No. 60/832,727, filed on Jul. 20, 2006.

(51) Int. Cl.
*A61K 31/335*   (2006.01)
*A61K 31/55*   (2006.01)

(52) U.S. Cl.
CPC ............ *A61K 31/335* (2013.01); *A61K 31/55* (2013.01); *Y10S 514/923* (2013.01)

(58) Field of Classification Search
CPC .................................................. Y10S 514/923
See application file for complete search history.

(56) References Cited

U.S. PATENT DOCUMENTS

| | | |
|---|---|---|
| 3,420,851 A | 1/1969 | Bloom et al. |
| 3,438,981 A | 4/1969 | Stach |
| 3,509,175 A | 4/1970 | Tretter |
| 4,110,438 A | 8/1978 | Gahwyler |
| 4,434,171 A | 2/1984 | Müller |
| 4,833,154 A | 5/1989 | Jean-Louis et al. |
| 5,030,632 A | 7/1991 | Sterling |
| 5,116,852 A | 5/1992 | Gammans |
| 5,332,661 A | 7/1994 | Adamczyk et al. |
| 5,502,047 A | 3/1996 | Kavey |
| 5,585,115 A | 12/1996 | Sherwood et al. |
| 5,643,897 A | 7/1997 | Kavey |
| 5,725,883 A | 3/1998 | Staniforth |
| 5,725,884 A | 3/1998 | Sherwood et al. |
| 5,733,578 A | 3/1998 | Hunter et al. |
| 5,741,524 A | 4/1998 | Staniforth et al. |
| 5,858,412 A | 1/1999 | Staniforth et al. |
| 5,866,166 A | 2/1999 | Staniforth et al. |
| 5,948,438 A | 9/1999 | Staniforth et al. |
| 5,965,166 A | 10/1999 | Hunter et al. |
| 6,016,865 A | 8/2000 | Staniforth et al. |
| 6,103,219 A | 8/2000 | Sherwood et al. |
| 6,211,229 B1 | 4/2001 | Kavey |
| 6,217,907 B1 | 4/2001 | Hunter et al. |
| 6,217,909 B1 | 4/2001 | Sherwood et al. |
| 6,219,674 B1 | 4/2001 | Classen |
| 6,344,487 B1 | 2/2002 | Kavey |
| 6,358,533 B2 | 3/2002 | Sherwood et al. |
| 6,391,337 B2 | 5/2002 | Hunter et al. |
| 6,395,303 B1 | 5/2002 | Staniforth et al. |
| 6,403,597 B1 | 6/2002 | Wilson et al. |
| 6,407,128 B1 | 6/2002 | Scaife et al. |
| 6,471,994 B1 | 10/2002 | Staniforth et al. |
| 6,521,261 B2 | 2/2003 | Sherwood et al. |
| 6,584,472 B2 | 6/2003 | Classen |
| 6,683,102 B2 | 1/2004 | Scaife et al. |
| 6,746,693 B2 | 6/2004 | Staniforth et al. |
| 6,852,336 B2 | 2/2005 | Hunter et al. |
| 6,858,231 B2 | 2/2005 | Sherwood et al. |
| 6,866,867 B2 | 3/2005 | Staniforth et al. |
| 6,936,277 B2 | 8/2005 | Staniforth et al. |
| 7,135,196 B2 | 11/2006 | Stockham |
| 7,179,488 B2 | 2/2007 | Sherwood et al. |
| 7,276,536 B2 | 10/2007 | Urata et al. |

(Continued)

FOREIGN PATENT DOCUMENTS

| | | |
|---|---|---|
| WO | 1999/040898 A2 | 8/1999 |
| WO | 2000/010554 A2 | 3/2000 |

(Continued)

OTHER PUBLICATIONS

Doxepin. Find Treatment & Support. The most reliable cancer treatment information. Cancer.org. Web download: Jul. 6, 2010 http://www.cancer.org/docroot/CDG/content/CDG doxepin.asp?internal=1. p. 1-6.

(Continued)

*Primary Examiner* — Kyle A Purdy

(74) *Attorney, Agent, or Firm* — Servilla Whitney LLC

(57) ABSTRACT

Methods of improving the pharmacokinetics of doxepin in a patient.

19 Claims, 1 Drawing Sheet

(56) References Cited

U.S. PATENT DOCUMENTS

| | | |
|---|---|---|
| 7,452,872 B2 | 11/2008 | Johnson |
| 7,915,307 B2 | 3/2011 | Casseday et al. |
| 8,097,625 B2 | 1/2012 | Lalji et al. |
| 2002/0037828 A1 | 3/2002 | Wilson et al. |
| 2002/0197235 A1 | 12/2002 | Moran |
| 2003/0206978 A1 | 11/2003 | Sherwood et al. |
| 2003/0235617 A1 | 12/2003 | Martino et al. |
| 2004/0063721 A1 | 4/2004 | Deecher et al. |
| 2004/0115142 A1 | 6/2004 | Sherwood et al. |
| 2004/0224017 A1 | 11/2004 | Mulye |
| 2004/0265374 A1 | 12/2004 | Staniforth et al. |
| 2005/0013861 A1 | 1/2005 | Sherwood et al. |
| 2005/0118261 A1 | 6/2005 | Oien et al. |
| 2005/0123609 A1 | 6/2005 | Hirsh et al. |
| 2005/0147673 A1 | 7/2005 | Staniforth et al. |
| 2005/0171160 A1 | 8/2005 | Edgar et al. |
| 2005/0196439 A1 | 9/2005 | Sherwood et al. |
| 2005/0214365 A1 | 9/2005 | Yousef et al. |
| 2005/0239838 A1 | 10/2005 | Edgar et al. |
| 2005/0256165 A1 | 11/2005 | Edgar et al. |
| 2006/0008522 A1 | 1/2006 | Staniforth et al. |
| 2006/0228487 A1 | 10/2006 | Schaible et al. |
| 2007/0281990 A1 | 12/2007 | Rogowski et al. |
| 2008/0058407 A1 | 3/2008 | Baron et al. |
| 2008/0058408 A1 | 3/2008 | Rogowski et al. |
| 2008/0182890 A1 | 7/2008 | Jochelson et al. |
| 2009/0042971 A1 | 2/2009 | Rogowski et al. |
| 2009/0042972 A1 | 2/2009 | Rogowski et al. |
| 2009/0074862 A1 | 3/2009 | Schioppi et al. |
| 2010/0105614 A1 | 4/2010 | Jochelson |
| 2010/0179214 A1 | 7/2010 | Dubé et al. |
| 2010/0179215 A1 | 7/2010 | Dubé et al. |
| 2010/0227916 A1 | 9/2010 | Kavey et al. |
| 2011/0077200 A1 | 3/2011 | Jochelson et al. |
| 2011/0166215 A1 | 7/2011 | Casseday et al. |
| 2011/0178166 A1 | 7/2011 | Rogowski et al. |
| 2011/0318412 A1 | 12/2011 | Schioppi et al. |
| 2012/0088822 A1 | 4/2012 | Rogowski et al. |
| 2012/0245222 A1 | 9/2012 | Rogowski et al. |

FOREIGN PATENT DOCUMENTS

| | | |
|---|---|---|
| WO | 2000050025 A1 | 8/2000 |
| WO | 2003/004009 A1 | 1/2003 |
| WO | 2007047519 A2 | 6/2003 |
| WO | 2003066029 A2 | 8/2003 |
| WO | 2007/136845 A3 | 11/2007 |
| WO | 2007142810 A2 | 12/2007 |
| WO | 2007142811 A2 | 12/2007 |

OTHER PUBLICATIONS

Lunesta (Eszopiclone) Tablets 1 mg, 2 mg, 3 mg. Prescribing Information. Package Insert. Sepracor Inc. Jan. 2009. p. 1-2.
National Academy of Sciences, Sleeping Pills, Insomnia, and Medical Practice, Institute of Medicine, 32-33, 103, 125, 149, 169, 198, (1979).
Natrol Melatonin 3 mg. 60 Tablets. Dietary Supplement. Manufactured by NATROL, Inc. LABEL. p. 1-3.
New Drug Application 16-798 for SINEQUAN approved in 1978 (includes evaluation of insomnia indication on pp. 46-47, 54, 57, 59.
NyQuil Cold & Flu. Nightime Relief. Acetaminophen, Doxylamine, Dextromethorphan, Alcohyl 10%. 6 Fl Oz. Vicks LABEL. 2 pages.
NyQuil Oral. Drugs & Medications. WebMD. Web download: Jul. 6, 2010. http://www.webmd.com/drugs/drug-6104-NyQuil+Oral. aspx?drugid=6104&drugname=NyQuil+Oral&source=1, p. 1-3.
Nytol Oral. Drugs & Medications—WebMD. Web download: Jul. 6, 2010. http://www. webmd. com/d rugs/d rug-10538-Nytol+Oral. aspx?drugid=10538&drugname=Nytol+Oral&source=O. p. 1-2.
Nytol Quickcaps with Diphenhydramine HCI. Nightime Sleep-Aid, 72 Caplets, LABEL. 4 pages.
Partial International Search Report dated Apr. 8, 2008 in PCT/US2007/082569, filed Oct. 25, 2007.
Patent Information Leaflet, Sinequan™ (doxepin), United Kingdom, p. 1-2 (2002).
Pfizer, Chemist Review of NOA 17-516, Division of Neuropharmacological Drug Products, Chemists Review #3, (1973).
Pharmaca Fennica. Published by the Finnish Centre for Medicine Information (Laaketietokeskus); SR Doxal; (1992).
Pharmaca Fennica. Published by the Finnish Centre for Medicine Information (Laaketietokeskus); SR Doxal; 612-613 (1988).
Pharmaca Fennica. Published by the Finnish Centre for Medicine Information (Laaketietokeskus); SR Doxal; 714 (1991).
Pharmaca Fennica. Published by the Finnish Centre for Medicine Information (Laaketietokeskus); SR Doxal; 830 (1995).
Pharmaca Fennica. Published by the Finnish Centre for Medicine Information (Laaketietokeskus); Ye R Doxal; 534-535 (2000).
Pharmaca Fennica. Published by the Finnish Centre for Medicine Information (Laakevalrnisteet); SR SINEQUAN; 845-846 (1993).
Pharmaca Fennica, Published by the Finnish Centre for Medicine Information (Laaketietokeskus); SR Doxal; 738 (1993).
Pharmaceuticals Announces FDA Approval of SILENOR® (Doxepin) for the 266 Treatment of Insomnia, Somaxon Pharmaceuticals Press Release, San Diego, CA, p. 1-5 (Mar. 18, 2010).
Pharmassure. Standardized. Valerian. Herbal Supplement. Minimumum 0.8% Valerenic 219 Acids (2mg). 250 mg. 60 Softgel Capsules. Distributed by PharmAssure, Inc. LABEL. p. 1-4.
Physician's Desk Reference, 1999 ed., Medical Economics Company, Montvale NJ pp. 539-541 (Trazadone).
Physician's Desk Reference, 2000 ed., Medical Economics Company, Montvale NJ pp. 2366-2367 (Doxepine HCI).
Physician's Desk Reference, 2000 ed., Medical Economics Company, Montvale NJ pp. 3323-3324 (Trimipramine maleate).
Physician's Desk Reference, 2000 ed., Medical Economics Company, Montvale NJ pp. 549-551 (Amitriptyline HCI).
Physicians Desk Reference, Litton Industries; p. 1211, 93, (1976).
Physicians' Desk Reference, p. 1310-1312, (1990).
Physicians' Desk Reference, p. 1849-1850, (1990).
Physicians' Desk Reference, p. 2434-2435, (1990).
Polish Drug Application for SINEQUAN 10 mg capsules. 01474/93, p. 1-4 with attached Annex in 4 pages.
Polish Drug Application for SINEQUAN 25 mg capsules. 01475/93. p. 1-4 with attached Annex in 4 pages.
Restoril—Temazepam capsule. Mallinckrodt Inc. Prescribing Information. Revised Mar. 2006. p. 1-8.
Rodenbeck et al., The sleep-improving effects of doxepin are paralleled by a normalized plasma cortisol secretion in primary insomnia, Psychopharma. 170(4): 423-428 (2003).
Rozerem (ramelteon) tablets. Highlights of Prescribing Information. Takeda Pharmaceuticals. Revised Oct. 2008. p. 1-6.
Seminar on Psychosomatics, Auspices of Academy of Psychosomatic Medicine, p. 4-63 (1968).
Silenor (doxepin) Prescribing Information. Revised Mar. 2010. p. 1-12.
Sinequan (doxepin HCI) Capsules Oral Concentrate. Prescribing Information. Revised Oct. 2008, p. 1-13.
Sinequan (Doxepin, Adapin): A guide to sinequan side effects. depression-guide.com.(2005). Web download: Jul. 6, 2010. http://www.depression-guide.com/sinequan.htm. p. 1-3.
Sinequan Dosage. eMEDTV, Clinaero, Inc. Updated/reviewed Apr. 2, 2007. Web download: Jul. 6, 2010. http://depression.emedtv.com/sinequan/sinequan-dosage.html. p. 1-2.
Somaxon Pharmaceuticals Announces Acceptance for Filing of New Drug Application for SILENOR™ for the Treatment of Insomnia, Somaxon Pharmaceuticals Press Release, San Diego, CA, p. 1-5 (Apr. 15, 2008).
Somaxon Pharmaceuticals Announces Completion of 26-Week Transgenic Mouse Carcinogenicity Study of SILENOR™, Somaxon Pharmaceuticals Press Release, San Diego, CA, p. 1-3 (Jan. 9, 2008).
Somaxon Pharmaceuticals Announces Data to be Presented at American Psychiatric Association 161st Annual Meeting, Somaxon Pharmaceuticals Press Release, San Diego, CA (May 2, 2008).

(56) References Cited

OTHER PUBLICATIONS

Somaxon Pharmaceuticals Announces Data to be Presented at American Psychiatric Association 161st Annual Meeting, Somaxon Pharmaceuticals Press Release, San Diego, CA, p. 1-7 (May 7, 2008).
Somaxon Pharmaceuticals Announces Positive Phase 3 Results with SILENOR™ for 267 theTreatment of Adults with Chronic Insomnia, Somaxon Pharmaceuticals, p. 1-5, (Apr. 10, 2006).
Somaxon Pharmaceuticals Announces Positive Results in a Phase II Dose-Finding Study of 268 Low-dose Doxepin in Adults with Primary Seep Maintenance Insomnia, Somaxon Pharmaceuticals, p. 1-2, (Jan. 6, 2005).
Somaxon Pharmaceuticals Announces Positive Results in a Phase II Dose-Finding Study of Low-Dose Doxepin in Elderly Patients with Primary Sleep Maintenance Insomnia, Somaxon Pharmaceuticals, p. 1-3, (Apr. 21, 2005).
Somaxon Pharmaceuticals Announces Presentation of Phase II SILENOR® Data at the Associated Professional Sleep Societies Annual Meeting, Somaxon Pharmaceuticals, p. 1-2, (Jun. 20, 2006).
Somaxon Pharmaceuticals Announces the Completion of Enrollment in a Phase II Study Evaluating S0-101 for the Treatment of Sleep Maintenance Insomnia in Adults, Somaxon Pharmaceuticals, p. 1, (Oct. 7, 2004).
Somaxon Pharmaceuticals Presents Analyses of Silenor Clinical Data at the American Psychiatric Association Annual Meeting, Somaxon Pharmaceuticals Press Release, San Diego, CA, p. 1-6 (May 20, 2009).
Somaxon Pharmaceuticals Presents Pharmacological Data on Doxepin at the 21st European College of Neuropsychopharmacology Congress, Somaxon Pharmaceuticals Press Release, San Diego, CA, p. 1-3 (Sep. 2, 2008).
ABPI (Association of the British Pharmaceutical Industry) Compendium of Data Sheets & SmPC's, 1999-2000; Pfizer Limited, p. 1158.
ABPI (Association of the British Pharmaceutical Industry) Compendium of Data Sheets and Summaries of Product Characteristics, 1996-1997; Pfizer Limited, p. 751-752.
ABPI (Association of the British Pharmaceutical Industry) Data Sheet Compendium 1991-1992; Pfizer Limited, p. 1147-1149.
ABPI (Association of the British Pharmaceutical Industry) Data Sheet Compendium 1993-1994; Pfizer Limited, p. 1205-1207.
ABPI (Association of the British Pharmaceutical Industry) Data Sheet Compendium 1994-1995; Pfizer Limited, p. 1150-1151.
ABPI (Association of the British Pharmaceutical Industry) Data Sheet Compendium 1995-1996; Pfizer Limited, p. 1239-1240.
ABPI (Association of the British Pharmaceutical Industry) Data Sheet Compendium 1998-1999; Pfizer Limited, p. 970-971.
ABPI (Association of the British Pharmaceutical Industry) Medicines Compendium, 2002; Pfizer Limited, p. 1792-1793.
Adapin, Drug Side Effects, <http://www.depression-guide.com/adapin.htm>, 2005, 1-3.
Albemarle Pulmonary Medicine Associates, <http://apmanc.com/PatientEducation/INSOMNIA.HTM>, 2000, pp. 1-4.
Ambien (Zolpidem Tartrate) tablets CIV. Highlights of Prescribing Information. Revised Jun. 2009. Sanofi-Aventis U.S. LLC. p. 1-18.
Ambien (Zolpidem Tartrate) tablets CIV. Prescribing Information. Revised Jun. 2008. Sanofi-Aventis U.S. LLC. p. 1-22.
Ambien CR (zolpidem tartrate extended-release). Highlights of Prescribing Information. Package Insert. Jan. 2008, Sanofi-Aventis U.S. LLC. p. 1-7.
Ambien CR (zolpidem tartrate extended release) tablets—CIV. Full Prescribing Information. Sep. 2009. Web download: Jul. 6, 2010. <http://products.sanotiaventis.us/ambien cr/ambiencr.html>. p. 1-32.
Ambien CR (zolpidem tartrate extended release). Healthcare Professional Information. Healthcare Professionals. Help your insomnia patients meet the day on. Web download: Jul. 6, 2010. <http://www.ambiencr.com/hcp/zolpidem-tartrate.aspx>. p. 1-2.
BPAI decision issued Dec. 11, 2012 in U.S. Appl. No. 11/804,720, filed May 18, 2007.

CBS.com, Ambien May Prompt Sleep-Eating; <http://www.cbsnews.com/stories/2006/03/15/early show/health/> (2 pages).
Chloral Hydrate Drug Information, Professional. Chloral Hydrate (Systemic). Drug Information Online. Drugs.com. Web download: Jul. 6, 2010. <http://www.drugs.com/mmx/chloral-hydrate.html>. p. 1-15.
Civil Docket of the U.S. District Court, District of Delaware, Case #1 :11-cv-00537-RGA-MPT, printed Dec. 21, 2012 Involving U.S. Pat. Nos. 6,211,229 and 7,915,307 of Somaxan Pharmaceuticals, Inc., pp. 1-5.
Council on Drugs, Evaluation of Doxepin Hydrochloride (Sinequan), JAMA, 215(12): 1967-68 (Mar. 22, 1971).
Doxal. Laakeopas. Retrieved Nov. 28, 2005 from <http://www.coronaria.fi/www/mtv3/laakkeet.php?id=299>.
Doxal. Laakkeet. Retrieved Nov. 28, 2005 from http: <www.tohtori.fi/laakkeet/tuote.php3?1D=412>.
Electronic File History of U.S. Appl. No. 11/804,722, filed May 18, 2007 (Abandoned) containing Office Action(s) dated Jun. 15, 2010, Nov. 8, 2010 and Jun. 2, 2011 and Applicant Response(s) filed Oct. 15, 2010.
Electronic File History of U.S. Appl. No. 11/867,595, filed Oct. 4, 2007 containing Office Action(s) dated Oct. 21, 2010, and May 10, 2011 and Applicants Response(s) filed Apr. 20, 2011, Sep. 30, 2011, Nov. 10, 2011 and Jul. 11, 2012 as of Sep. 26, 2012.
Electronic File History of U.S. Appl. No. 12/022,628, filed Jan. 30, 2008 containing Office Action(s) dated Mar. 6, 2009 and Nov. 20, 2009—abandoned.
Electronic File History of U.S. Appl. No. 12/022,788, filed Jan. 30, 2008 containing Office Action(s) dated Mar. 9, 2009 and Dec. 9, 2009—abandoned.
Electronic File History of U.S. Appl. No. 12/102,985, filed May 6, 2011 (Abandoned) containing Office Action(s) dated Mar. 16, 2012 and Applicant(s) submissions Dec. 22, 2011 and Sep. 17, 2012 abandoned.
Electronic File History of U.S. Appl. No. 12/301,457, filed Apr. 12, 2010 containing Office Action(s) dated Jun. 7, 2012 and Applicants Response(s) filed Apr. 12, 2010 and Nov. 29, 2012 as of Dec. 17, 2012.
Electronic File History of U.S. Appl. No. 12/976,866, filed Dec. 27, 2010 (Abandoned) containing Office Action(s) dated Oct. 19, 2011 and Dec. 8, 2011 and Applicants Response filed Sep. 30, 2011.
German Federal Gazette (BAnz) No. 240 of Dec. 22, 1992, p. 9545 (vol. 44).
Guidance for Industry SUPAC-IR/MR: Immediate Release and Modified Release Solid Oral Dosage Forms—Manufacturing Equipment Addendum, Jan. 1999.
International Preliminary Report on Patentability & Written Opinion dated Apr. 7, 2009 in PCT/US2007/080492, filed Oct. 4, 2007.
International Preliminary Report on Patentability & Written Opinion dated Jan. 20, 2009 in PCT/US2007/016464, filed Jul. 20, 2007.
International Preliminary Report on Patentability & Written Opinion dated Nov. 21, 2008 in PCT/US2007/012105, filed May 18, 2007.
International Preliminary Report on Patentability & Written Opinion dated Nov. 21, 2008 in PCT/US2007/012106, filed May 18, 2007.
International Preliminary Report on Patentability & Written Opinion dated Nov. 21, 2008 in PCT/US2007/012107, filed May 18, 2007.
International Preliminary Report on Patentability and Written Opinion dated Jun. 18, 2009 in PCT/US2007/086682, filed Dec. 6, 2007.
International Preliminary Report on Patentability dated Dec. 4, 2008 in PCT/US2007/011893, filed May 18, 2007.
International Preliminary Report on Patentability dated Oct. 13, 2009 in PCT/US2008/060131, filed Apr. 11, 2008.
International Search Report and Written Opinion dated Aug. 13, 2009 in PCT/US2009/042912, filed May 5, 2009.
International Search Report and Written Opinion dated Jan. 19, 2008 in PCT/US2008/060131, filed Apr. 11, 2008.
International Search Report and Written Opinion dated Jan. 21, 2008 in PCT/US2007/012107, filed May 18, 2007.
International Search Report and Written Opinion dated Jul. 29, 2008 in PCT/US2007/086682, filed Dec. 6, 2007.

(56) References Cited

OTHER PUBLICATIONS

International Search Report dated Aug. 11, 2007 in PCT/US2007/011893, filed May 18, 2007.
International Search Report dated Dec. 10, 2007 in PCT/US2007/016464, filed Jul. 20, 2007.
International Search Report dated Jan. 24, 2008 in PCT/US2007/012105, filed May 18, 2007.
International Search Report dated Jan. 24, 2008 in PCT/US2007/012106, filed May 18, 2007.
International Search Report dated Jun. 17, 2008 in PCT/US2007/080492, filed Oct. 4, 2007.
International Search Report dated Mar. 18, 2008 in PCT/US2007/082569, filed Oct. 25, 2007.
Seifritz, Contribution of Sleep Physiology to Depressive Pathophysiology, Neuropsychopharmacology 25(5) S1: S85-S88 (Nov. 2001).
Shu, et al., Identification of Phenolic Doxepin Glucuronides from Patient Urine and Rat Bile. Drug Metab Disp. 18(6): 1096-1099 (1990).
Shu, et al., The Identification of Urinary Metabolites of Doxepin in Patients. Drug Metabolism & Disposition, Drug Metabolism & Disposition, 18(5): 735-741 (1990).
Sokoliess, et al., Separation of (Z)- and (E)-isomers of thioxanthene and dibenz[b,e]oxepin derivatives with calixarenes and resorcinarenes as additives in nonaqueous capillary eiectrophoresis. Electrophoresis. 24(10):1648-57 (2003).
Stella, et al., "Prodrugs: Challenges and Rewards Part 1", Biotechnology: Pharmaceutical Aspects, 2007, p. 24.
Stimmel, et al., Mirtazapine: An Antidepressant with Noradrenergic and Specific Serotonergic Effects Pharmacotherapy, (1997) 17(1): 10-21.
Thase, Antidepressant Treatment of the Depressed Patient with Insomnia, J. Clin. Psychiatry (1999) 60(Suppl. 17): 28-31.
Vincent, et al., Use of Human Sleep as a Test of Drug's Psychotropic Action with Doxepin as an example, Bordeaux Medical, No. 10, 2650-51, 2653-54, 2657-57, and 2661, (1971).
Voshaar, et al., Zolpidem is not Superior to Temazepam with Respect to Rebound Insomnia: A Controlled Study. Eur Neuropsychopharmacol. 14(4): 301-306 (2004).
Ward, et al., Doxepin plasma levels and therapeutic response in depression: preliminary findings. J Clin Psychopharmacol. 2(2):126-8 (1982).
Ware, Tricyclic Antidepressants in the Treatment of Insomnia, Journal of Clinical Psychiatry; 44 [9, Section 2]: 25-28 (1983).
Wheatley, Prescribing Short-Acting Hypnosedatives: Current Recommendations from a Safety Perspective, Drug Safety 7(2):106-115 (1992).
Wolfe, Antidepressant Withdrawal Reactions. Am Fam Physician. 56(2): 455-462, (1997).
Wyatt, et al., Carbon13 NMR of Z- and E-Doxepin Hydrochloride. Applied Spectroscopy. 49(4):538-542 (1986).
Yan, et al., Stereoselective and simultaneous measurement of cis- and trans-isomers of 314 doxepin and N-desmethyldoxepin in plasma or urine by high-performance liquid chromatography. J Chromatogr B Biomed Sci Appl. 691(1):131-8 (1997).
Yan, et al., Stereoselective in vivo and in vitro studies on the metabolism of doxepin and Ndesmethyldoxepin. Xenobiotica. 27(12): 1245-1257 (1997).
Ziegler, et al., Doxepin kinetics. Clin Pharrnacol Ther. 23(5):573-9 (1978).
Zimmermann, et al., "Epidemiology, implications and mechanisms underlying drug-induced weight gain in psychiatric patients" J. Psychiatric Research (2003) 37: 193-220.
Zung, Effect of Antidepressant Drugs on Sleeping and Dreaming, Excerpta Medica Foundation International Congress Series, No. 150, 1824-1826, (1968).
International Preliminary Report on Patentability dated May 7, 2009 in PCT/US2007/082569, filed Oct. 25, 2007.
Becker, Pharmacologic and Nonpharmacologic Treatments of Insomnia, Neural Clin. 23: 1149-1163 (2005).

Biggs, et al., Dosage schedule and plasma levels of doxepin and desmethyldoxepin. J Clin Psychiatry. 39(10):740-2 (1978).
Bogaert, et al., Plasma levels of the cis- and trans-isomers of doxepin and desmethyldoxepin after administration of doxepin to patients. Arzneimittelforschung. 31(1):113-5 (1981).
Brunello, et al., Effect of Some Tricyclic and Nontricyclic Antidepressants on [H]Imiipramine Binding and Serotonin Uptake in Rat Cerebral Cortex After Prolonged Treatment. Fundam Clin Pharmacol. 1: 327-333 (1987).
Brunswick, et al., Relationship between tricyclic antidepressant plasma levels and clinical 120 response in patients treated with desipramine or doxepin. Acta Psychiatr Scand. 67(6):371-7 (1983).
Bundgaard, "Ed. Design of Prodrugs; Bioreversible derivatives for various functional groups and chemical entities", Elsevier, Amsterdam, Chapter 1, 1985, 1-92.
Burch, et al., Amitriptyline pharmacokinetics. A crossover study with single doses of amitriptyline and nortriptyline, Psychopharmacology (Berl), 1981; 74(1):35-42.
Charman, Lipids, Lipophilic Drugs, and Oral Drug Delivery-Some Emerging Concepts. J Pharm Sci .89(8):967-78 (2000).
Chen, Sleep, Depression and Antidepressants, British Journal of Psychiatry, 135: 385-402, (1979).
Claudino, et al., Antidepressants for Anorexia Nervosa (Review). Cochrane Database Syst Rev., John Wiley & Sons, Ltd., 1 :1-39 (2006).
Conn, et al., Pattern of Use of Antidepressants in Long-Tern Care Facilities for the Elderly, Journal of Geriatric Psychiatry and Neurology, vol. 5:4, p. 228-232, (1992).
Declerck, et al., Increase in Slow-wave Sleep in Humans with the Serotonin-S2 Antagonist Ritanserin. CurrTher Res., 41(4): 427-432 (1987).
Desyrel, trazadone hydrochloride tablet. Bristol-Myers Squibb Company. Prescribing Information. Revised Feb. 2009. p. 1-9.
Deuschle, et al., Doxepin and its Metabolites in Plasma and Cerebrospinal fluid in Depressed Patients, Psychopharmacology, 131 (1): 19-22, (1997).
Dilger, et al., High-performance liquid chromatographic determination of trans-doxepin and desmethyldoxepin. Arzneimittelforschung. 38(10): 1525-8 (1988).
Dugovic, et al., 5-HT2 Receptors could be Primarily Involved in the Regulation of Slowwave Sleep in the Rat. Euro J Pharma., 137: 145-146 (1987).
Dunleavy, et al., Changes During Weeks in Effects of Tricyclic Drugs on the Human Sleeping Brain, British Journal of Psychiatry, 120: 663-672, (1972).
Ebert, et al., Treating Insomnia: Current and investigational pharmacological approaches. Pharmacol Thera., 112(3): 612-629 (Mar. 2006).
Elavil, Amitriptyline Hydrochloride—amitriptyline hydrochloride tablet, film coated. Mutual Pharmceutical Company, Inc. Revised Sep. 2007. p. 1-9.
Ereshefsky, et al., Pharmacokinetic factors affecting antidepressant drug clearance and 140 clinical effect: evaluation of doxepin and imipramine—new data and review. Clin Chem. 34(5):863-80 (1988).
Erman, et al., Comparative Efficacy of Zolpidem and Temazepam in Transient Insomnia, Human Psychopharma Clin Exp., 16: 169-176 (2001).
Faulkner, et al., Comparative assays for doxepin and desmethyldoxepin using high-performance liquid chromatography and high-performance thin-layer chromatography. J Pharm Sci. 72(10):1165-7 (1983).
Faulkner, et al,, Multiple-dose doxepin kinetics in depressed patients. Clin Pharmacol Ther. 34(4):509-15 (1983).
Fava, Weight Gain and Antidepressants. J Clin Psychiatry., (61 Suppl) 11: 37-41, (2000).
Fawcett, et al,, Review of the Results from Clinical Studies on the Efficacy, Safety and Tolerability of Mirtazapine for the Treatment of Patients with Major Depression J. Affective Disorders (1998) 51: 267-285.
Friedel, et al., "Relationship of blood levels of sinequan to clinical effects in the treatment 146 of depression in aged patients". In. Mendels J, editor. Amsterdam: Excerpta Medica. p. 51-53 (1975).

(56) References Cited

OTHER PUBLICATIONS

Fulton, et al., Assessment of the Antidepressant Activity of Dothiepin and its Metabolites by Preclinical Tests. J Affect Dis. 4: 261-269 (1982).
Georgotas, et al., Response of Depressive Symptoms to Nortiptyline, Phenelzine and Placebo, Br. J. Psychiatry (1987) 151: 102-106.
Ghabrial, et al., Geometric isomerization of doxepin during its N-demethylation in humans. Drug Metab Dispos. 19 (3):596-9 (1991).
Gillin, et al., Successful Separation of Depressed, Normal, and Insomniac Subjects by EEG Sleep Data, Arch Gen Psychiatry, vol. 36, p. 85-90, (1979).
Green, Clinical importance of doxepin antidepressant plasma levels. J Clin Psychiatry. 39(5):481-2 (1978).
Grundstrom, et al., Sedative Properties of Doxepin in Comparison with Diazepam, Psychopharmacology, 54: 165-169 (1977).
Hajak, et al., Nocturnal Melatonin Secretion and Sleep after Doxepin Administration in Chronic Primary Insomnia; Pharmacopsychiatry 29: 187-192, (1996).
Halcion, Triazolam tablet. Pharmacia and Upjohn Company. Prescribing Information. Revised Jan. 2009. p. 1-10.
Haritos, et al., Role of cytochrome P450 2D6 (CYP2D6) in the stereospecific metabolism of E- and Z-doxepin. Pharmacogenentics, 10(7):591-603 (2000).
Haritos, et al., Stereoselective measurement of E- and Z-doxepin and its N-desmethyl and hydroxylated metabolites by gas chromatography-mass spectrometry. J Chromatogr B Biomed Sci Appl. 736(1-2):201-8 (1999).
Hartmann, Clinical Pharmacology—Miratzapine: A Newer Antidepressant, American Family Physician (1999) 1-5.
Hartmann, et al., The Effects of Long Term Administration of Psychotropic Drugs on Human Sleep: 111. The Effects of Amitriptyline, Psychopharmacologia, 33: 185-202 (1973).
Hartter, et al., The N-demethylation of the doxepin isomers is mainly catalyzed by the polymorphic CYP2C19. Pharm Res. 19(7):1034-7 (2002).
Haute Autorite De Sante (France), "XP002507207 (Online) Retrieved from the Internet: URL: <http://www.has-sante.fr/potrail/jcms/c_475580/quitaxon> retrieved Dec. 8, 2003".
Heal, et al., Comparative Pharmacology of Dothiepin, its Metabolites, and other Antidepressant Drugs. Drug Dev Res. 27: 121-135 (1992).
Hellberg, et al., The Hydrolysis of the Prostaglandin Analog Prod rug Bimatoprost to 17-Phenyl-Trinor PGF2 by Human and Rabbit Ocular Tissue. J Ocul Pharmacol Ther., 19(2): 97-103 (2003).
Higuchi, et al., Pro-Drugs as Novel Delivery Systems, A.C.S. Symposium Series, American Chemical Society; vol. 14, (1975)—Title Pages Only.
Hobbs, Distribution and Metabolism of Doxepin, Biochem. Pharmacol., 18(8): 1941-1954, (1969).
Hohagen, et al., Treatment of Primary Insomnia with Trimiprarnine: An Alternative to Benzodiazepine Hypnotics? Eur Arch Psychiatry Clin Neurosci. 244(2): 65-72 (1994).
Hrdina, et al., Antidepressant plasma levels and clinical response in depressed patients treated with oxaprotiline and doxepin. Int Clin Psychopharmacol. Jul.;3(3),205-14 (1988).
Hrdina, et al., Cis- and trans-isomers of doxepin and desmethyldoxepin in the plasma of depressed patients treated with doxepin. Ther Drug Monit. 12(2):129-33 (1990).
Hsu, et al., Low-Dose Doxepin in the treatment of primary insomnia, Sleep, 28: suppl, p. A50, (2005).
Jacobsen, Low-Dose Trazodone as a Hypnotic in Patients Treated with MAOIs and Other Psychotropics: A Pilot Study, Journal of Clinical Psychiatry, 51: 298-392 (1990).
Joyce, et al., Doxepin plasma concentrations in clinical practice. Could there be a pharmacokinetic explanation for low concentrations? Clin Pharmacokinet. 10(4):365-70 (1985).
Kales, et al., Effects of Sinequan on sleep of Insomniac Subjects, Sleep Study Abstracts, p. 93, (1972).
Kirchheiner, et al., Contributions of CYP2D6, CYP2C9 and CYP2C19 to the biotransformation of E- and Z-doxepin in healthy volunteers. Pharmacogenetics, 12(7):571-80 (2002).
Kline, et al., Doxepin and Desmethyldoxepin Serum Levels and Clinical Response. In: Gottschalk LA MM, editor. Pharmacokinetics of psychoactive drugs: blood levels and clinical response. New York: Spectrum Press. p. 221-228 (1976).
Krakowski, Seminar on Psychopharmacology—Auspices of Academy of Psychosomatic Medicine, Dec. 8-9, 1968 Freeport, Grand Bahama Island, Psychosomatics, pp. 7-63 (1968).
Laimer, et al., Effect of Mirtazapine Treatment on Body Composition and Metabolism, J Clin Psychiatry, 67(3): 421-524 (2006).
Lapp, Chronic Fatigue Syndrome is a Real Disease, North Carolina Family Physician, 43:1, (1992).
Leucht, et al., Doxepin plasma concentrations: is there really a therapeutic range? J Clin Psychopharmacol. 21 (4):432-9 (2001).
Linnoila, et al., Clomipramine and doxepin in depressive neurosis. Plasma levels and therapeutic response. Arch Gen Psychiatry. 37(11):1295-9 (1980).
Luchtefeld, Answers to the Most Common Questions Regarding Prescription Drugs—Safeguard Your Health, Jenry Consulting 1999, <http://www.grandtimes.com/Answer Drugs.html>, 1-3.
Luo, et al., The Quaternary Ammonium-Linked Glucuronide of Doxepin: A Major Metabolite in Depressed Patients treated with Doxepin. Drug Metab Dispos., 19(3): 722-724, (1991).
Manning, et al., Central Nervous System Effects of Meclizine and Dimenhydrinate: Evidence of Acute Tolerance to Antihistamines. J. Clin. Psychiatry 32:996-1002 (1992).
Masaki, et al., Involvement of Hypothalamic Histamine H1 Receptor in the Regulation of Feeding Rhythm and Obesity, Diabetes 53(9): 2250-2260, (2004).
Masaki, et al., The Hypothalamic H1 Receptor: A Novel Therapeutic Target for Disrupting Diurnal Feeding Rhythm and Obesity. Trends Pharmacol Sci. 27(5): 279-284, (2006).
Mayers, et al., Antidepressants and their effect on sleep, Hum Psychopharmacol., 20(8):533-559 ( Dec. 2005).
Mealy, et al., "Drugs Under Development for the Treatment of Psyciatric Distorders", Drugs Fut. 31(3), 2006, 266-284.
Mercer, et al., Dietary Induced Anorexia: A Review of Involvement of the Histominergic System, J Am Coll Nutr., 15(3): 223-230, (1996).
Midha, et al., Stereoselective pharmacokinetics of doxepin isomers. Eur J Clin Pharmacol. 42(5):539-44 (1992).
Moody, et al.; Biotransformation of Doxepin by Cunninghamella E/egans; Drug Metab Dispo., 27(10): 1157-1164, (1999).
Narasimhachari, et al., N-Alkylation of Secondary Amine Tricyclic Antidepressants as a General Method for Their Quantitation by GC-MS-SIM Technique. Analytical Lett. 12(B1):77-88 (1979).
Neubauer, Sleep Problems in the Elderly. Am Fam Physician. 59(9): 2551-2558 (May 1999).
Newcomer, et al., The Metabolic Effects of Antipsychotic Medications, Can J Psychiatry. 51 (8): 480-491 (2006).
Nicholson, et al., Modulation of sleep by trimipramine in man, European Journal of Clinical Pharmacol, 37: 145-150, (1989).
Nierenberg, et al., Management of Monoamine Oxidase Inhibitor-Associated Insomnia with Trazodone, Journal of Clinical Psychopharmacol, vol. 9 No. 1, p. 42-45, (1989).
O'Brien, et al., GLC determination of doxepin plasma levels. J Pharm Sci. 65(7):1068-9 (1976).
Ookuma, et al., Evidence for Feeding Elicited Through Antihistaminergic Effects of Tricyclic Antidepressants in the Rat Hypothalamus, Psychopharmacology (Berl). 101 (4): 481-485, (1990).
Orthen-Gambill, Antihistaminic Drugs Increase Feeding, While Histidine Suppresses Feeding in Rats, Pharmacol Biochem Behav., 31(1): 81-86, (1988).
Orthen-Gambill, et al., Differential Effects of Psychotropic Drugs on Feeding in Rats: Is Histamine Blockade Involved? Pharmacol Biochem Behav., 36(4): 837-841 (1990).
Palvimaki, et al., Interactions of selective serotonin reuptake inhibitors with the serotonin 5-HT2C receptor. Phychopharmacology, 126(3): 234-240 (1996).
Pecknold, et al., Trimipramine, Anxiety, Depression and Sleep, Drugs, vol. 38: Suppl. 1, p. 25-31, (1989).

(56) References Cited

OTHER PUBLICATIONS

Phillips, et al., Sleep Disorders in the Elderly, Sleep Medicine 2: 99-114 (2001).
Pinder, et al., "Doxepin Up-to-Date: A Review of its Pharmacological Properties and Therapeutic Efficacy with Particular Reference to Depression", Drugs 13, 1977, 161-218.
Pollack, Is Biotechnology Losing Its Nerve?, NY Times (Feb. 29, 2004), pp. 1-4.
Pollack, et al., The Selective GABA Reuptake inhibitor Tiagabine for the Treatment of Generalized Anxiety Disorder: Results of a Placebo-Controlled Study, J Clin Psychiatry 66:1401-1408 (Nov. 2005).
Powell, et al., Compendium of Excipients for Parenteral Formulations, PDA J Pharm Sci Technol. 52(2): 238-311 (1998).
Prakash, et al., Deuterium Labelling of the Antidepressant Drug Doxepin for Disposition Studies in Human Subjects. J Lab Comp Radiopharma. 28(9): 1037-47 (1990).
Remington, "The Science and Practice of Pharmacy", 21st Ed. Lippincott Williams and Wilkins. Table of Contents Only., 2006.
Ribbentrop, et al., Pharmacologic studies of doxepin, an antidepressive agent with centrally anticholinergic and sedative effects. Arzneimitteiforschung. 15:863-68 (1965). Translation of Abstract only.
Richardson, et al., Tolerance to Daytime Sedative Effects of H1 Antihistamines. J Clin Psychopharmacol. 22(5): 511-515 (2002).
Richelson, Tricyclic Antidepressants and Histamine H1 Receptors, Mayo Clin Proc., 54:669-67 4, (1979).
Richelson, et al., Antagonism by Antidepressants of Neurotransmitter Receptors of Normal Human Brain in Vitro, J Pharmacol Exp Ther. 230(1): 94-102 (1984).
Roche, Bioreversible Carriers in Drug Design: Theory and Application, Pergamon Press: New York, pp. 14-21 (1987)—Contents Pages Only.
Rosseel, et al., Quantitative GLC determination of cis- and trans-isomers of doxepin and desmethyldoxepin. J Pharm Sci. 67(6):802-5 (1978).
Roth, et al., Efficacy and Safety of Doxepin 1 mg, 3mg , and 6mg in Adults with Primary Insomnia, Sleep, 30(11): 1555-1561 (Nov. 2007).
Roth, et al., Efficacy and Safety of doxepin 1, 3 , and 6mg in elderly adults with primary insomnia, Sleep (Rochester),29: suppl. S (2006).
Roth, et al., Efficacy and Safety of Zolpidern-MR: A Double-Blind, Placebo-Controlled Study in Adults with Primary Insomnia, Sleep Med. 7(5): 397-406 (2006).
Roth, et al., Psychopharmacolodgy: The Effects of Doxepin HCl on Sleep and Depression, Journal of Clinical Psychiatry, 43:9, p. 366-368 (1982).
Saul, Study Links Ambler Use to Unconscious Food Forays, The New York Times http://www.nytimes.com/2006/03/14/health/14sleep.html (4 pages).
Scharf, et al., Efficacy and Safety of Doxepin 1 mg, 3 mg, and 6 mg in Elderly Patients 249 With Primary Insomnia: A Randomized, Double-Blind, Placebo-Controlled Crossover Study. J Clin Psychiatry 69(10): 1557-1564 (Oct. 2008).
Schatzberg, et al., "Hypnotics" Manual of Clinical Psychopharmacology, American Psychiatric Press, Inc., Washington D.C., p. 173-189, (1986).
Schweitzer, et al., Sleepiness and Performance During Three-Day Administration of Cetirizine or Diphenhydramine. J Allergy Clin Immunol. 94(4): 716-724 (1994).
Somaxon Pharmaceuticals Provides Update on New Drug Application for SILENOR® (Doxepin) for the Treatment of Insomnia, Somaxon Pharmaceuticals Press Release, San Diego, CA, p. 1-4 (Apr. 7, 2009).
Somaxon Pharmaceuticals Provides Update on New Drug Application for SILENOR® for the Treatment of Insomnia, Somaxon Pharmaceuticals Press Release, San Diego, CA, p. 1-3 (Jan. 21, 2010).
Somaxon Pharmaceuticals Provides Update on Preclinical and Clinical Programs for SILENOR™, Somaxon Pharmaceuticals Press Release, San Diego, CA, p. 1-3 (Sep. 11, 2006).
Somaxon Pharmaceuticals Provides Update on SILENOR® Development Program for the Treatment of Insomnia, Somaxon Pharmaeuticais, p. 1-5, (Jul. 19, 2006).
Somaxon Pharmaceuticals Provides Update on SILENOR™ Development Program, Somaxon Pharmaceuticals Press Release, San Diego; CA, p. 1-3 (May 9, 2007).
Somaxon Pharmaceuticals Provides Update on SILENOR™ Preclinical Program, Somaxon Pharmaceuticals Press Release, San Diego, CA, p. 1-7 (Feb. 13, 2007).
Somaxon Pharmaceuticals Receives Complete Response Letter from the FDA for SILENOR® (Doxepin), Somaxon Pharmaceuticals Press Release, San Diego, CA, p. 1-3 (Feb. 26, 2009).
Somaxon Pharmaceuticals Receives Complete Response Letter from the FDA for SILENOR® NOA, Sornaxon Pharmaceuticals Press Release, San Diego, CA, p. 1-3 (Dec. 7, 2009).
Somaxon Pharmaceuticals Resubmits New Drug Application for SILENOR® (Doxepin) for the Treatment of Insomnia, Somaxon Pharmaceuticals Press Release, San Diego, CA, p. 1-4 (Jun. 4, 2009).
Somaxon Pharmaceuticals Scheduled to Meet with FDA to Discuss Complete Response Letter for SILENOR® NOA, Somaxon Pharmaceuticals Press Release, San Diego, CA (Dec. 17, 2009).
Somaxon Pharmaceuticals' SILENOR® Data Presented at the 22nd Annual Meeting of the Associated Professional Sleep Societies, Somaxon Pharmaceuticals Press Release, San Diego, CA, p. 1-4 (Jun. 12, 2008).
Somaxon Pharmaceuticals' SILENOR™ Demonstrates Positive Results in a Phase 3 Transient Insomnia Clinical Trial, Somaxon Pharmaceuticals, p. 1-5, (Oct. 23, 2006).
Somaxon Pharmaceuticals' SILENOR™ Demonstrates Positive Results in its Third Phase 3 Clinical Trial in Insomnia, Somaxon Pharmaceuticals, p. 1-6, (Nov. 20, 2006).
Somaxon Pharmaceuticals Submits New Drug Application for SILENOR™ for the Treatment of Insomnia, Somaxon Pharmaceuticals Press Release, San Diego, CA, p. 1-6 (Jan. 31, 2008).
Somaxon Pharmaceuticals to Present Data at the 22nd Annual Meeting of the Associated Professional Sleep Societies, Somaxon Pharmaceuticals Press Release, San Diego, CA (Jun. 4, 2008).
Somaxon Pharmaceuticals, Inc. Initiates Phase III Clinical Trials of SILENOR™ in Patients with Insomnia, Somaxon Pharmaceuticals Press Release, San Diego, CA, p. 1-3 (Jun. 9, 2005).
Somaxon Pharmaceuticals, Inc. Initiates Second Phase III Clinical Trials of SILENOR™, Somaxon Pharmaceuticals Press Release, San Diego, CA (Sep. 20, 2005).
Somaxon Pharmaeuticals Announces the Completion of Enrollment in a Phase II Study 291 Evaluating S0-101 for the Treatment of Sleep Maintenance Insomnia in Adults, Somaxon Pharmaceuticals, p. 1, (Oct. 7, 2004).
Somaxon's SILENOR™ Demonstrates Positive Results in Long-Term Phase 3 Clinical Trial in Elderly Patients with Insomnia, Somaxon Pharmaceuticals, p. 1-7, (Dec. 18, 2006).
Sominex Caplets. Nightime sleep-aid—Diphenhydramine. GlaxoSmithKline. Consumer Healthcare, L.P. LABEL. 3 pages.
Sominex Oral. Drugs & Medications. WebMD. Web download: Jul. 6, 2010. <http://www.webmd.com/drugs/drug-15470-Sominex+Oral.aspx?drugid=15470&drugname=Sominex+Oral&source=1> p. 1-3.
Sonata (Zaleplon) Capsules. Prescribing Information. King Pharmaceuticals. Feb. 2009. p. 1-15.
Sonata Official FDA information, side effects and uses. Drug Information Online, Drugs.com. Web. Jul. 6, 2010. <http://www.drugs.com/pro/sonata.html> p. 1-22.
Summary Basis for approval of ADAPIN (1972) Pursuant to FOIA Request filed in 1981.
Summary Basis for approval of SINEQUAN® (1973) Pursuant to FOIA Request filed in 1973 (sedative, tranquilizer and sleep effects mentioned for example on pp. 50, 54-56, 58-59).
Technical Information/Summary of Drug Characteristics (SPC), Pfizer, p. 1-4, (2004).
Tylenol PM Extra Strength Pain Reliever. Nighttime Sleep Aid. Contains Acetaminophen, Diphenhydramine HCl. 24 Geltabs. LABEL. 4 pages.

(56) References Cited

OTHER PUBLICATIONS

Tylenol PM Oral. Drugs & Medications—WebMD. Web download: Jul. 6, 2010, http://www.webmd.com/drugs/drug-74986-Tylenol+PM+Oral.aspx?drugid=7 4986&drugname=Tylenol+PM+Oral&source=1, p. 1-3.
Tylenol PM. Extra Strength Pain Reliever, Nighttime Sleep Aid. Contains Acetaminophen, Diphenhydramine HCl. 50 Caplets. LABEL. 4 pages.
Virtanen et al., Radioimmunoassay for doxepin and desmethyldoxepin., Acta Pharmacol Toxicol (Copenh). 47(4):274-8 (1980).
Zaleplon Capsules. Drug Information Online. Drugs.com. Web download: Aug. 25, 316 2009. Retrieved from the interenet: <http://www.drugs.com/pro/zaleplon.html?printable=1> and Package Label. Augobindo Pharma Ltd, p. 1-23.
Adapin, 2005, 3 pages.
Approval data of the German drug regulatory authorities. DIMDI: AMIS—Public Part (AJ29). German Institute of Medical ocumentation and Information within the scope of the Fed. Ministry of Health. Pfizer Pharma GmbH. Singuan10 mg; capsules Sinquan 25 Intramuscular; solution; Sinquan 25 mg; capsules, Sinquan 50 mg; capsules, Sinquan 75 mg; capsules. Retrieved Nov. 16, 2005 from <https://gripsdb.dimdi.de/session/051116152129299204 7 /13docs.htm>.
Electronic File History, of U.S. Appl. No. 12/446,914, filed May 27, 2010 containing Office Action(s) dated Aug. 5, 2011, Jan. 20, 2012, Feb. 17, 2012 and Sep. 5, 2012 and Applicants Response(s) filed May 27, 2010, Jan. 20, 2012, and Aug. 17, 2012 as of Sep. 25, 2012.
Electronic File History of U.S. Appl. No. 11/781,165, filed 0712012007 (USP 7,915,307,338 issued Mar. 29, 2011) containing, Office Action(s) dated Oct. 14, 2008, 0710712009, 0912912009, 2-part Apr. 6, 2010, Oct. 21, 2010 and Nov. 12, 2010 and Applicant Response(s) filed Apr. 14, 2009, document Dec. 4, 2009, Jul. 6, 2010 and Oct. 21, 2010 as of Sep. 14, 2012.
Final Office Action in U.S. Appl. No. 11/781,165, dated Nov. 12, 2010, 3 pages.
Insomnia, 2000, 4 pages.
Non-Final Office Action in U.S. Appl. No. 11/781,165, dated Apr. 6, 2010, 10 pages.
Non-Final Office Action in U.S. Appl. No. 11/781,165, dated Jul. 7, 2009, 14 pages.
Prescription drugs, 1999, 3 pages.
SILENOR (doxepin) Drug Description, RX List, Apr. 2, 2010, 1 page.
Sinequan Label, Pfizer, Jun. 2014, 14 pages.
Sinequan Label, Pfizer, May 2007, 13 pages.
Abernethyl, et al., Absolute bioavailability of imipramine: Influence of food, Psychopharmacology (Berl), 1984; 83(1):104-106.
Adamzyk, et al., Quantitative determination of E- and Z-doxepin and E- and Z-desmethyldoxepin by high-performance liquid chromatography. Ther Drug Monit. 17(4):371-6 (1995).
Anocili-Isreal, et al., "Identification and Treatment of Sleep Problems in the Elderly Review Article", Sleep Medicine Reviews 1(1), 1997, 3-17.
Anon, "Quitaxon 10 mg cp pellic sec. Online", XP002507206, retrieved from the Internet: URL:http://www.vidal.fr/medicament/wuitaxon-14133.htm on Dec. 8, 2008.
Badenhorst, et al., Determination of doxepin and desmethyldoxepin in human plasma using liquid chromatography-tandem mass spectrometry. J Chromatogr B Biomed Sci Appl. 742(1):91-8 (2000).
Baldrick, Pharmaceutical excipient development: the need for preclinical guidance. Regul Toxicol Pharmacol. 32(2): 210-218 (2000).

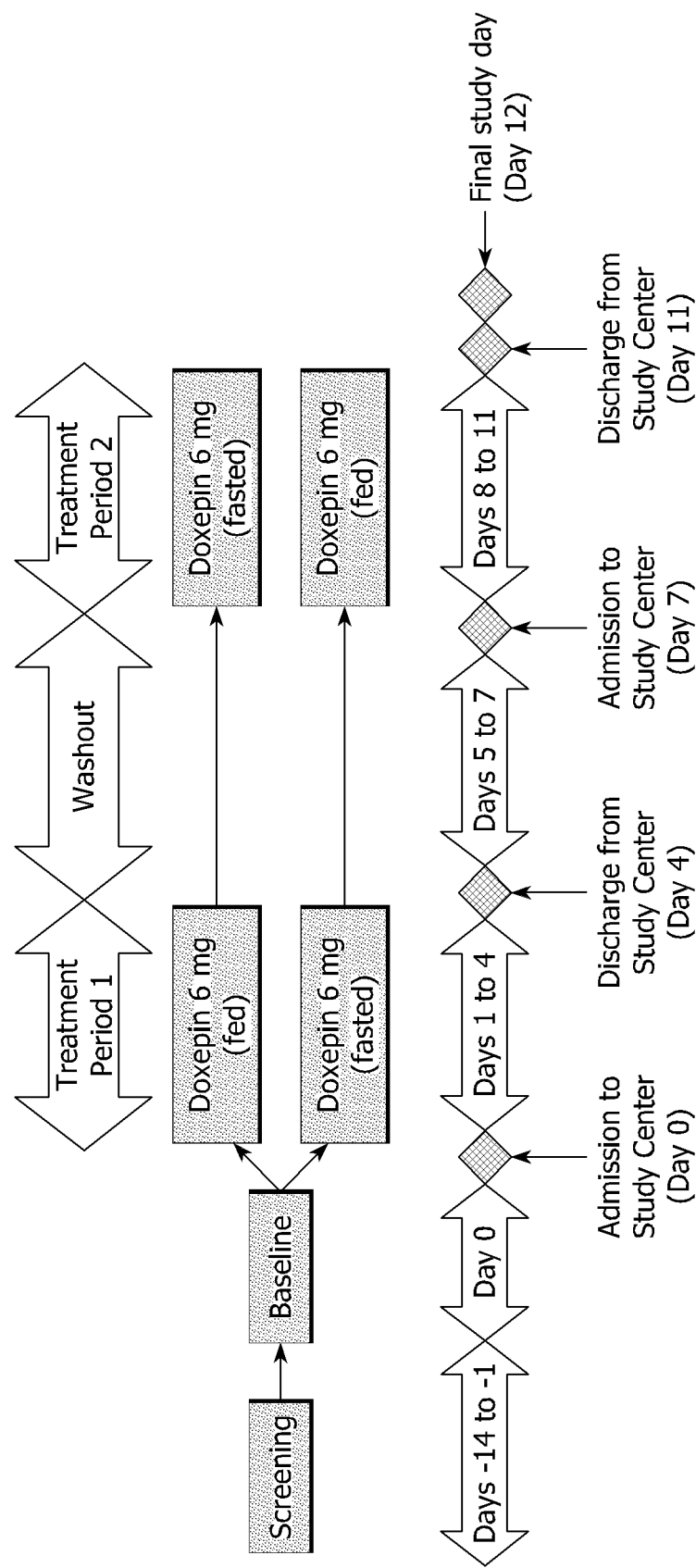

METHODS OF IMPROVING THE PHARMACOKINETICS OF DOXEPIN

CROSS-REFERENCE TO RELATED APPLICATIONS

This application is a continuation of U.S. application Ser. No. 13/007,334, filed Jan. 14, 2011, which is a continuation of U.S. application Ser. No. 11/781,165, filed Jul. 20, 2007, which claims priority to U.S. Provisional Application Nos. 60/832,727 and 60/833,617, respectively filed on Jul. 20, 2006 and Jul. 24, 2006, both entitled METHODS OF IMPROVING THE PHARMACOKINETICS OF DOXEPIN. The disclosure of each of the above-described applications is hereby incorporated by reference in its entirety.

FIELD OF THE INVENTION

The present invention relates to methods of improving the pharmacokinetics of doxepin in a patient.

BACKGROUND OF THE INVENTION

The term "food effect" refers to a somewhat unpredictable phenomenon that can influence the absorption of drugs from the gastrointestinal tract following oral administration. A food effect can be designated "negative" when absorption is decreased, or "positive" when absorption is increased and manifested as an increase in oral bioavailability (as reflected by total exposure, usually defined as AUC). Alternatively, food effects can refer to changes in maximum concentration ($C_{max}$), or the time to reach maximum concentration ($T_{max}$), independently of overall absorption. As a result, some drugs have to be taken in either fasted or fed conditions to achieve the optimum effect. For example, patients may be instructed to take a drug with a meal, before a meal (e.g., one hour before a meal), or after a meal (e.g., two hours after a meal). However, many drugs are unaffected by food, and thus, can be taken in either a fasted or a fed condition.

Doxepin is a tricyclic compound currently approved for treatment of depression and anxiety. The recommended daily oral dose for the treatment of depression or anxiety ranges from 75 milligrams to 300 milligrams. Also, U.S. Pat. Nos. 5,502,047 and 6,211,229 describe the use of doxepin for the treatment chronic and non-chronic (e.g., transient/short term) insomnia. Doxepin, unlike most FDA-approved products for the treatment of insomnia, is not a Schedule IV controlled substance. Historically, doxepin pharmacokinetics have not been known to be affected by food.

In treating depression, anxiety and sleep disorders it is beneficial to optimize the pharmacokinetics of the administered medication in a patient. For example, in the case of sleep disorders a patient may have a set window of time within which they desire that their sleep occur. Thus, it can be useful to minimize the amount of time required to attain a maximum concentration of a drug in order to receive the therapeutic benefit of the drug as soon as possible during the desired treatment period.

SUMMARY OF THE INVENTION

Some embodiments are based upon the surprising discovery about the food effects of doxepin. For example, as described more fully below, it has been discovered that administration of doxepin without food decreases the time to achieve maximum blood concentration or $T_{max}$ for doxepin. In one experiment, the administration of doxepin without food resulted in achieving $T_{max}$ three hours more quickly than when doxepin was administered with food. As another example, it has been discovered that administration of doxepin with food increases the overall bioavailability of doxepin and results in a higher maximum concentration ($C_{max}$) of doxepin. In one experiment, the administration of doxepin with food resulted in a 41% increase in bioavailability ($AUC_{0-\infty}$) and a 15% increase in $C_{max}$ compared to administration in a fasted state.

As a result of the various discoveries related to the food effects of doxepin and depending upon the type of therapy and the desired overall result of that therapy, a patient can benefit from a number of different therapeutic regimens. Disclosed are various therapeutic regimens influenced by the food effects observed with doxepin.

Achieving a More Rapid Maximum Concentration ($T_{max}$)

In some circumstances, more rapid onset of doxepin action may be desired. One embodiment relates to a method of shortening the time required to achieve a maximum plasma concentration of doxepin in a patient receiving doxepin therapy, which method can include administering to the patient a therapeutically effective amount of doxepin in a pharmaceutical composition without food. The methods can have various benefits, including more rapid onset of drug action, shorter duration of effect, etc. The administration to the patient can occur, for example, at least about 30 minutes, at least about 1 hour, at least about 2 hours, at least about 3 hours or at least about 4 hours, or more after consuming food. Also, administration to the patient can occur at least about 30 minutes, at least about 1 hour, at least about 2 hours, at least about 3 hours, or at least about 4 hours, or more prior to consuming food, for example.

Sleep Therapy:

Another embodiment relates to methods of treating sleep disorders. A desirable sleep medication preferably can have the ability to affect the onset of drug action and the duration of drug activity (e.g., to avoid hangover, etc.). Generally, a person will desire to fall asleep as soon as possible, to stay asleep for about 8 hours, and to wake up without hangover or extra sedation at the end of the 8 hours. As mentioned above, surprisingly, the administration of doxepin without food resulted in achieving a maximum concentration of the drug three hours sooner compared to administration with food. As a result, when treating sleep, doxepin can be taken without food in order to achieve earlier onset of drug action and/or a shorter duration of drug action.

Thus, some embodiments relate to a method of shortening the time required to achieve sleep onset, which method can include administering to the patient a therapeutically effective amount of doxepin in a pharmaceutical composition without food. Also, another embodiment relates to a method of treating a sleep disorder comprising providing a patient with a therapeutically effective amount of doxepin and providing the patient with instructions to take the doxepin without food. The doxepin can be provided to the patient at least about 30 minutes, at least about 1 hour, at least about 2 hours, at least about 3 hours or at least about 4 hours or more after consuming food, or at least about 30 minutes, or at least about 1 hour prior to consuming food.

Still a further embodiment relates to a method of treating a sleep disorder comprising providing a patient with a therapeutically effective amount of doxepin and providing the patient with information regarding a doxepin food effect. The information can be provided orally or in written form. Some exemplary written forms include a label associated with the drug, on the container for the drug, packaged with the drug, or separately given to the patient apart from the drug.

Still some embodiments relate to the use of doxepin in the preparation of a medicament for treatment of a sleep disorder, said medicament for administration without food. Also, the use can further be for shortening the time required to achieve a maximal plasma concentration of doxepin by administration without food. The administration without food can occur when the patient is in a fasted state. The administration without food can occur, for example, at least about 30 minutes, at least about 1 hour, at least about 2 hours, at least about 3 hours or at least about 4 hours, or more after consuming food. Also, it can occur, for example, at least about 30 minutes, at least about 1 hour, at least about 2 hours, at least about 3 hours, or at least about 4 hours, or more prior to consuming food. In some aspects, the administration of the doxepin can occur, for example, at least about 30 minutes, at least about 1 hour, or more prior to consuming food.

Achieving a Greater $C_{max}$ or a Greater Bioavailability

Greater $C_{max}$:

Some embodiments relate to a method of increasing the maximum plasma concentration of doxepin in a patient receiving doxepin therapy comprising administering to the patient a therapeutically effective amount of doxepin in a pharmaceutical composition with food.

Greater Bioavailability:

Also, some embodiments relate to methods of increasing the oral bioavailability of doxepin, including by administering to a patient an amount of a pharmaceutical oral dosage form of doxepin with food. Further embodiments relate to methods of increasing the oral bioavailability of doxepin to a patient receiving doxepin therapy, which methods can include administering to the patient an amount of a pharmaceutical oral dosage form of doxepin with food, wherein the administration results in an $AUC_{0-\infty}$ that is greater than that achieved by the administration of the same amount of doxepin without food. In such methods, the doxepin can be administered as part of a chronic doxepin therapy, for example.

Anxiety/Depression Therapy:

Still another embodiment relates to methods of treating depression or anxiety. It is worth noting that improved pharmacokinetics of doxepin in the context of depression or anxiety can be beneficial, for example by, leading to more safe and effective dosing. The methods of treating depression or anxiety can include administering a therapeutically effective amount of doxepin preferably with food. In some embodiments the depression or anxiety can be treated by administering doxepin without food. Also, some embodiments relate to methods of treating depression or anxiety, including by providing a patient with a therapeutically effective amount of doxepin and providing the patient with instructions to preferably take the doxepin with food. In some alternative embodiments, the instructions can specify taking the doxepin without food.

Another embodiment relates to a method of treating depression or anxiety comprising providing a patient with a therapeutically effective amount of doxepin and providing the patient with information regarding a doxepin food effect.

Also, some embodiments relate to the use of doxepin in the preparation of a medicament for treatment of a psychological disorder, said medicament for administration with food. The disorder can preferably be depression or anxiety. The use also can be for the preparation of a medicament for increasing the oral bioavailability of doxepin by administration with food; for increasing the oral bioavailability of doxepin to a patient receiving doxepin therapy by administering an amount of a pharmaceutical oral dosage form of doxepin with food, wherein the administration results in an $AUC_{0-\infty}$ that is greater than that achieved by the administration of the same amount of doxepin without food; for increasing the time required to achieve a maximal plasma concentration of doxepin by administration with food; for minimizing side effects associated with a doxepin treatment of the psychological disorder, by administering a therapeutically effective amount of doxepin with food, which can result in the patient receiving or in a physician prescribing a lower dosage of doxepin compared the dosage that is taken by the patient without food; or for improving the consistency of pharmacokinetics associated with doxepin therapy, in which a patient receives a multiple doxepin dosages over multiple days, comprising administering the doxepin in a fixed temporal relationship to food intake by the patient.

Decreasing Bioavailability:

It should be noted that some embodiments relate to methods of decreasing the oral bioavailability of doxepin. Decreasing oral bioavailability can be beneficial in some contexts. For example, as mentioned above for sleep therapies, it can be beneficial to shorten the duration of the drug action in order to minimize hangover or other effects. The methods of decreasing bioavailability can include administering to a patient an amount of a pharmaceutical oral dosage form of doxepin without food. Furthermore, some embodiments relate to methods of decreasing the oral bioavailability of doxepin to a patient receiving doxepin therapy, comprising administering to the patient an amount of a pharmaceutical oral dosage form of doxepin without food, wherein the administration results in an $AUC_{0-\infty}$ that is less than that achieved by the administration of the same amount of doxepin with food. In such methods, doxepin can be administered as part of a chronic doxepin therapy, for example. Also, in such methods administration to the patient can occur, for example, at least about 30 minutes, at least about 1 hour, at least about 2 hours, at least about 3 hours or at least about 4 hours, or more after consuming food. Also, administration to the patient can occur at least about 30 minutes, at least about 1 hour, at least about 2 hours, at least about 3 hours, or at least about 4 hours, or more prior to consuming food, for example.

Minimizing Doxepin Side Effects and Improving Pharmacokinetic Consistency

Some embodiments relate to methods of minimizing side effects associated with a doxepin therapy. The methods can include, for example, administering a therapeutically effective amount of doxepin to a patient with food. Also, the administration of doxepin with food can result in a patient receiving or a physician prescribing a lower dose of doxepin compared to the dosage prescribed without food.

This disclosure includes a method for improving the consistency of pharmacokinetics associated with doxepin therapy, in which a patient receives multiple doxepin dosages over multiple days, comprising administering the doxepin to the patient in a fixed temporal relationship to food intake by the patient. This can, for example, include providing written or verbal instructions to the patient to take the doxepin in a fixed temporal relationship to food intake by the patient. Taking doxepin in a fixed relationship to food can help assure more consistent efficacy of the medication.

Other Food Effect Methods

Also, some embodiments relate to methods of alleviating a doxepin food effect or altering a doxepin pharmacokinetic parameter in a patient, for example, by administering doxepin to a patient in need thereof, wherein the patient is in a non-fasted state or in a fasted state.

Further embodiments relate to a method of treating a disorder with doxepin comprising providing a patient with a therapeutically effective amount of doxepin and providing the patient with information regarding a doxepin food effect. The information can include, for example, instructions to take the doxepin with or without food, or to ensure that doxepin is consistently taken either with or without food. The information can be in an oral or written form. Some exemplary written forms include a label associated with the drug, on the container for the drug, packaged with the drug, separately given to the patient apart from the drug, or provided in manner that the patient can independently obtain the information (e.g., a web site).

Dosage and Compositions

Again, in the various disclosed embodiments, the amount of doxepin, including the therapeutically effective amount, may advantageously be, for example, about 0.001 milligram to about 350 milligrams, preferably about 50 milligrams to about 300 milligrams or more preferably about 75 milligrams to about 300 milligrams, or any amount or sub-range within those ranges. Alternatively, the effective amount may be about 0.5 milligrams to about 20 milligrams, more preferably about 1 milligram to about 6 milligrams.

Also, in the various disclosed embodiments, the pharmaceutical composition of doxepin can be, for example, a tablet, capsule or liquid. Furthermore, the doxepin can be provided or administered as a unit dosage form. Preferably, the doxepin can be provided or administered as an oral dosage form.

Doxepin Kits and Products

Finally, the present disclosure also includes a kit or a product that includes doxepin and written instructions or information associated therewith to take the doxepin without food. For example, the instructions can specify that doxepin be administered to the patient at least about 30 minutes, at least about 1 hour, at least about 2 hours, at least about 3 hours, at least about 4 hours or more after consuming food, or at least about 30 minutes, at least about 1 hour, at least about 2 hours, at least about 3 hours, at least about 4 hours or more prior to consuming food, for example. In some aspects, the kits or product can include instructions that describe administration to the patient preferably at least about 30 minutes or at least about 1 hour prior to consuming food. The kit or product can include information regarding a food effect associated with doxepin. Alternatively, it includes a kit or a product comprising doxepin and written instructions associated therewith to take the doxepin with food.

The product or kit can include doxepin in amount of about 0.5 milligram to about 350 milligrams, preferably about 50 milligrams to about 300 milligrams or more preferably about 75 milligrams to about 300 milligrams. Alternatively, the amount may be about 0.5 milligrams to about 20 milligrams, more preferably about 1 milligram to about 6 milligrams. Some preferred amounts are about 1 milligram, about 3 milligrams and about 6 milligrams.

Finally, the product or kit can include doxepin as a tablet, a capsule, a liquid, a unite dosage form or an oral dosage form, for example.

BRIEF DESCRIPTION OF THE DRAWINGS

FIG. 1 illustrates the design of a study of food effect associated with doxepin.

DETAILED DESCRIPTION OF THE INVENTION

Embodiments described herein relate to the novel and unexpected discovery of a food effect associated with doxepin. As described more fully below, a single-center, phase 1, randomized, open-label, single dose, two-way crossover study was conducted in 16 healthy young adult male and female volunteers. A food effect was observed on the pharmacokinetics of doxepin. In the fed state, pharmacokinetic parameters ($AUC_{0-\infty}$ and $C_{max}$) of doxepin were approximately 41% and 15% higher, respectively, compared to the fasted state, and median $T_{max}$ was delayed by approximately 3.0 hours in the fed state. The increase in AUC was statistically significant and demonstrates a positive food effect on exposure. The increased $T_{max}$ in the fed state suggests that food slows the absorption of the drug.

Accordingly, some embodiments relate to methods of improving the pharmacokinetics of doxepin in a patient. As discussed above and more fully elsewhere herein, administration of doxepin in a fasted state can result in decreasing the time required to achieve a maximum plasma concentration of doxepin. In particular, the time to reach maximum concentration ($T_{max}$) of doxepin can be minimized by administering the drug without food. Also, as discussed above and more fully elsewhere herein, administration of doxepin with food can increase the overall bioavailability of the drug. For example, the time to reach maximum concentration can be increased by administering doxepin with food and the bioavailability of the drug can be increased.

In addition, in a different embodiment, the total effective amount of drug that the patient receives can be maximized by administering doxepin with food, while in other embodiments the oral bioavailability of doxepin can be decreased by administering the doxepin without food. Because plasma concentrations and half-lives of doxepin are already known to vary from patient to patient, knowledge of the doxepin food effect can help patients and physicians to eliminate this additional source of dosing uncertainty, to improve safety and tolerability, and improve therapies that utilize doxepin. For example, as described more fully elsewhere herein, depending on the effect desired, doxepin can be taken with food; it can be taken after the patient has gone without food for a period of time; and/or it can be taken some period of time prior to consuming food.

As a result of the food effect discovery, various improved therapeutic methods are provided, including: where short term exposure is desired, with a more rapid onset and shorter duration of effect, doxepin preferably can be taken without food; in order to increase the bioavailability of the drug where rapid onset and shorter duration are not issues, doxepin preferably can be taken with food; and to assure more consistent efficacy, doxepin preferably can be taken in a fixed relationship to food consumption, regardless of whether the drug is taken with our without food. Short term exposure with more rapid onset can be preferable when treating, for example, a sleep disorder, while increased bioavailability and/or consistent kinetics can be preferable for treating conditions such as depression and anxiety.

Doxepin HCl is a tricyclic compound currently approved for treatment of depression and anxiety. The recommended daily dose for the treatment of depression or anxiety ranges from 75 milligrams to 300 milligrams. Also, U.S. Pat. Nos. 5,502,047 and 6,211,229, the entire contents of which are incorporated herein by reference, describe the use of doxepin for the treatment chronic and non-chronic (e.g., transient/short term) insomnias at dosages below those used to treat depression. A food effect associated with doxepin treatment of currently approved disorders or sleep disorders has not previously been reported.

Methods of Improving the Pharmacokinetics of Doxepin

Some embodiments relate to methods of improving the pharmacokinetics of doxepin, including by administering doxepin with or without food. A number of pharmacokinetic parameters can be affected by taking doxepin with or without food, including for example, $T_{max}$, $C_{max}$, and the area under the curve (AUC). Furthermore, various therapeutic regimens can be utilized to take advantage of the doxepin food effects.

Affecting Maximum Concentration ($T_{max}$):

As discussed above, administration of doxepin without food or in a fasted state can result in shortening the time required to achieve a maximum plasma concentration ($T_{max}$) of doxepin. Achieving a shorter $T_{max}$ can be desirable since onset of drug action can be more rapid and the duration of drug action may be shortened. Some embodiments relate to methods of shortening the time required to achieve a maximum plasma concentration or a $T_{max}$ of doxepin in a patient receiving doxepin therapy, which methods can include administering to the patient a therapeutically effective amount of doxepin in a pharmaceutical composition without food.

Also, it should be noted that other embodiments relate to methods of increasing the time required to achieve a maximum concentration of doxepin in a patient by administering doxepin with food.

Some embodiments relate to methods of preventing a doxepin food effect in order to minimize the time required for onset of action of the drug. The methods can include administering doxepin to a patient in need thereof, wherein the patient is in a fasted state or has not eaten or will not eat within a particular time period. The methods further can include providing instructions to take the doxepin without food or in a fasted state.

Use of Doxepin in Sleep Related Indications:

Knowledge of the food effect disclosed herein is useful in determining an optimum regimen for providing doxepin sleep therapy. In patients receiving sleep therapy, the onset of action is an important consideration. The studies disclosed herein demonstrate that taking doxepin with food can significantly increase $T_{max}$. As a result, sleep patients who take doxepin without food would be expected to have faster sleep onset or faster drug action in comparison to those who take doxepin with food.

Thus, some embodiments relate to improved methods of treating a sleep disorder. The methods can include providing a patient with a therapeutically effective amount of doxepin and providing the patient with instructions to take the doxepin without food. In some aspects, doxepin can be administered without food in order to minimize the amount of time to achieve sleep onset or to otherwise minimize the amount of time before drug action occurs.

The information regarding the doxepin food effect can be provided to the patient. The information can include, for example, instructions that may be provided to patients receiving doxepin therapy or health care professionals involved in treatment of those patients that the doxepin should be administered without food, preferably separated from food for the time periods discussed above. By way of example, such instructions could be provided orally or in written form. Some exemplary written forms include a label associated with the drug, on the container for the drug, packaged with the drug, or separately given to the patient apart from the drug, including providing the patient with access to a website or other electronic information with the instructions/information.

Affecting Overall Concentration ($C_{max}$) or Bioavailability:

The maximum plasma concentration or overall bioavailability of doxepin can be affected by food or a lack thereof. Increasing concentration or bioavailability can be desirable in some circumstances. Some embodiments relate to methods of increasing the oral bioavailability of doxepin to a patient receiving doxepin therapy. The methods can include administering to the patient a pharmaceutical oral dosage form of doxepin with food. The administration can result in a greater AUC than if the drug is taken without food. The methods can include administering to the patient a therapeutically effective amount of doxepin in a pharmaceutical composition with food or within a relatively short time of consuming food (e.g., 15 minutes, 30 minutes, one hour, etc.).

Also, some embodiments relate to a method of increasing the maximum plasma concentration of doxepin in a patient receiving doxepin therapy comprising administering to the patient a therapeutically effective amount of doxepin in a pharmaceutical composition with food.

It should be noted that other embodiments relate to methods of decreasing the oral bioavailability or AUC of doxepin by administering doxepin without food.

Use of Doxepin in Depression and Anxiety

Doxepin has been used for several decades in the treatment of depression and anxiety. Several side effects have been reported in connection with the use of doxepin to treat depression or anxiety. The studies disclosed herein show that by taking doxepin with food, AUC was increased by 41% compared to taking doxepin in a fasted state. Because AUC (bioavailability) is increased by taking doxepin with food, a patient can take a lower dose compared to when a patient takes doxepin without food. Increasing the oral bioavailability or AUC of doxepin, and decreasing dosage required for treatment can minimize or alleviate side effects and improve the safety and tolerability of doxepin therapy. Thus, in some aspects it can be preferred that patients receiving doxepin for depression or anxiety should take the drug with food, or in close proximity to eating. Some embodiments relate to improved methods of treating depression and anxiety. The methods can include providing a patient with a therapeutically effective amount of doxepin and providing the patient with instructions to take the doxepin with food. As discussed more fully herein, administering doxepin with food can result in an increase in the bioavailability of doxepin. As a result a patient can take less doxepin, which can be safer and more tolerable for the patient.

In some aspects, information, including instructions may be provided to patients receiving doxepin therapy or health care professionals involved in treatment of those patients regarding a doxepin food effect and/or that the doxepin should be administered with food, or at least in relatively close proximity to eating food or eating a meal (for example, within one hour or less). By way of example, such information or instructions could be provided orally or in written form. Some exemplary written forms include a label associated with the drug, on the container for the drug, packaged with the drug, or separately given to the patient apart from the drug, including providing the patient with access to a website or other electronic information with the instructions/information. The invention further includes a package of doxepin with such written instructions associated therewith.

It should be noted that some aspects of the invention also relate to methods of treating depression or anxiety by administering doxepin without food. Such embodiments can also include instructions to take the medication without food.

Improved Pharmacokinetic Consistency and Efficacy:

Still further embodiments relate to methods for improving the consistency of pharmacokinetics associated with doxepin therapy, in which a patient receives a multiple doxepin dosages over multiple days. The methods can include administering the doxepin to the patient in a fixed temporal relationship to food intake by the patient. Also, the method can further include providing instructions to the patient to take the doxepin in a fixed temporal relationship to food intake by the patient. As discussed more fully herein, taking doxepin in fixed or consistent temporal relationship to food can lead to improved safety and tolerability for the patient, for example, due to less variability in the drug kinetics in the patient.

Kits and Products:

Furthermore, some embodiments relate to kits and products for a therapy that includes the use of doxepin. The kits and products can include doxepin and instructions to take the doxepin without food or in a fasted state, or to take the doxepin with food or within a predetermined period of eating food.

The instructions or information regarding a food effect can be provided orally or verbally, or could be in written form. Some exemplary written forms include a label associated with the drug, on the container for the drug, packaged with the drug, or separately given to the patient apart from the drug, including providing the patient with access to a web site or other electronic information with the instructions/information. The invention further includes a package of doxepin with such written instructions associated therewith or with information on where to access the instructions/information (e.g., a website).

Administration of Doxepin

In performing the methods, doxepin, a pharmaceutically acceptable salt of doxepin, or prodrug of doxepin can be administered in any suitable oral form. Also, doxepin, or a pharmaceutically acceptable salt or a prodrug thereof can be administered to a patient. (It should be understood that the term "administer" and its variants are intended to cover both self-administration and administration by another person or by a device.).

Doxepin can be administered without food or in a fasted state. For example, doxepin can be administered at least about 30 minutes to about 4, 5, 6 or more hours after consuming food. More preferably, doxepin can be taken at least about 1 hour to about 6 hours after consuming food. In some aspects doxepin can be taken at least about 1, 2, 3, 4, 5, 6 or more hours after consuming food.

Also, doxepin can be administered at least about 30 minutes to about 6 hours before consuming any food, or more preferably, at least about 1 hour to about 3 hours before consuming food. In some aspects, doxepin can be administered about 1, 2, 3 or more hours before food is consumed.

In some embodiments of the invention, such as when doxepin is used to facilitate sleep, instructions may be provided to patients receiving doxepin therapy or health care professionals involved in treatment of those patients that the doxepin should be administered without food, preferably separated from food for the time periods discussed above. Also, the patient can be provided with information regarding a doxepin food effect. In other embodiments of the invention, such as when doxepin is used to treat depression or anxiety, instructions may be provided to patients receiving doxepin therapy or health care professionals involved in treatment of those patients that the doxepin should be administered with food, or at least in relatively close proximity to eating food or eating a meal (for example, within one hour or less).

Again, by way of example, such instructions or information regarding a food effect could be provided orally or verbally, or could be in written form. Some exemplary written forms include a label associated with the drug, on the container for the drug, packaged with the drug, or separately given to the patient apart from the drug, including providing the patient with access to a website or other electronic information with the instructions/information. The invention further includes a package of doxepin with such written instructions associated therewith.

It should be recognized that in some cases, the food effect disclosed herein can appropriately play a part in designing customized dosing regimens that reflect the preferences of a particular healthcare professional or their patient. Thus, for example, in doxepin therapy (e.g., chronic doxepin therapy), such as therapy for depression or anxiety, it is customary to titrate the dosage; in other words, typically start with a lower dose and then increase it to the minimum dose that is sufficiently effective for the patient in question. In this type of situation, there may be instances when doxepin is administered without food, even though more drug will be required to achieve the same effect. In such cases, consistency is important to maintaining equivalent pharmacological effects. In other words, if a patient on chronic doxepin therapy is receiving a titrated dose that has been determined when the patient is consistently taking doxepin with food, or consistently taking doxepin without food, then food-induced variations in doxepin pharmacokinetics should not be a factor in therapeutic response or side effects. Thus, for chronic doxepin therapy, one embodiment includes administering doxepin in a consistent relationship to food intake, regardless of whether it is or is not taken with food.

Suitable routes of administration of doxepin can include any route in which significant quantities of drug reach the stomach, including oral, buccal, and sublingual administration.

For oral administration, the compounds can be formulated readily by combining the active compounds with pharmaceutically acceptable carriers well known in the art. Such carriers enable the compounds of the invention to be formulated as tablets, pills, dragees, capsules, liquids, gels, syrups, slurries, suspensions and the like, for oral ingestion by a patient to be treated. Administration though oral pathways can be accomplished, for example, using a capsule, a tablet, a granule, a spray, a syrup, a liquid, powder, granules, pastes (e.g., for application to the tongue). Oral administration can be accomplished using fast-melt formulations, for example. For example, rapidly-melting strips or sheets that include the drug and suitable excipients can be prepared that dissolve quickly in the mouth, using well-known formulation technology. For buccal or sublingual administration, the compositions may take any suitable form, for example, tablets or lozenges. Pharmaceutical preparations for oral use can be obtained by mixing one or more solid excipient with pharmaceutical combination of the invention, optionally grinding the resulting mixture, and processing the mixture of granules, after adding suitable auxiliaries, if desired, to obtain tablets or dragee cores.

Pharmaceutical preparations which can be used orally include for example, liquid solutions, powders, and suspensions in bulk or unit dosage forms. Also, the oral formulations can include, for example, pills, tablets, granules, sprays, syrups, pastes, powders, boluses, pre-measured ampules or syringes, push-fit capsules made of gelatin, as well as soft, sealed capsules made of gelatin and a plasticizer, such as glycerol or sorbitol. The push-fit capsules can contain the active ingredients in admixture with filler such as lactose, binders such as starches, and/or lubricants such as talc or magnesium stearate and, optionally, stabilizers. In soft capsules, the active compounds may be dissolved or suspended in suitable liquids, such as fatty oils, liquid paraffin, or liquid polyethylene glycols. In addition, stabilizers may be added. All formulations for oral administration should be in dosages suitable for such administration.

A variety of techniques for formulation and administration can be found in *Remington: The Science and Practice of Pharmacy* (20$^{th}$ ed., Lippincott Williams & Wilkens Publishers (2003)), which is incorporated herein by reference in its entirety.

Compositions

As mentioned above, doxepin, pharmaceutically acceptable salts, and/or prodrugs of the same can be used alone or in combination with other substances, such as for example, other insomnia or sleep medications, or with other medications that treat a primary illness. Doxepin alone or in combination with other drugs can be included as part of a composition. The compounds and compositions can include any suitable form of the compound for pharmaceutical delivery, as discussed in further detail herein.

The compositions and formulations disclosed herein also can include one or more pharmaceutically acceptable carrier materials or excipients. Such compositions can be prepared for storage and for subsequent administration. Acceptable carriers or diluents for therapeutic use are well known in the pharmaceutical art, and are described, for example, in the incorporated material of *Remington: The Science and Practice of Pharmacy* (20$^{th}$ ed, Lippincott Williams & Wilkens Publishers (2003)), which is incorporated herein by reference in its entirety. The term "carrier" material or "excipient" herein can mean any substance, not itself a therapeutic agent, used as a carrier and/or diluent and/or adjuvant, or vehicle for delivery of a therapeutic agent to a subject or added to a pharmaceutical composition to improve its handling or storage properties or to permit or facilitate formation of a dose unit of the composition into a discrete article such as a capsule or tablet suitable for oral administration. Excipients can include, by way of illustration and not limitation, diluents, disintegrants, binding agents, adhesives, wetting agents, polymers, lubricants, glidants, substances added to mask or counteract a disagreeable taste or odor, flavors, dyes, fragrances, and substances added to improve appearance of the composition. Acceptable excipients include sugars (such as lactose, sucrose, mannitol, sorbitol), starch powder, maize starch, wheat starch, rice starch, potato starch, gelatin, gum tragacanth, methyl cellulose, hydroxypropylmethyl-cellulose, sodium carboxymethylcellulose, or derivatives thereof, cellulose esters of alkanoic acids, cellulose alkyl esters, talc, stearic acid, magnesium stearate, magnesium oxide, sodium and calcium salts of phosphoric and sulfuric acids, gelatin, acacia gum, sodium alginate, polyvinyl-pyrrolidone (PVP), and/or polyvinyl alcohol, saline, dextrose, lecithin, albumin, sodium glutamate, cysteine hydrochloride, and the like. Examples of suitable excipients for soft gelatin capsules include vegetable oils, waxes, fats, semisolid and liquid polyols. Suitable excipients for the preparation of solutions and syrups include, without limitation, water, polyols, sucrose, invert sugar and glucose. Suitable excipients for injectable solutions include, without limitation, water, alcohols, polyols, glycerol, and vegetable oils. If desired, the compositions can include disintegrating agents may be added, such as the cross-linked polyvinyl pyrrolidone, agar, or alginic acid or a salt thereof such as sodium alginate. The pharmaceutical compositions can additionally include preservatives, solubilizers, stabilizers, wetting agents, emulsifiers, sweeteners, colorants, flavorings, buffers, coating agents, or antioxidants. Compositions for oral administration can be formulated according to conventional pharmaceutical practice as described in the incorporated material in *Remington: The Science and Practice of Pharmacy* (20$^{th}$ ed, Lippincott Williams & Wilkens Publishers (2003)). For example, dissolution or suspension of the active compound in a vehicle such as water or naturally occurring vegetable oil like sesame, peanut, or cottonseed oil or a synthetic fatty vehicle like ethyl oleate or the like may be desired. Buffers, preservatives, antioxidants and the like can be incorporated according to accepted pharmaceutical practice. The compound can also be made in microencapsulated form.

One can also administer the compounds of the invention in sustained release forms or from sustained release drug delivery systems. A description of representative sustained release materials can be found in the incorporated materials in *Remington: The Science and Practice of Pharmacy* (20$^{th}$ ed, Lippincott Williams & Wilkens Publishers (2003)).

Dosage

The selected dosage level can depend upon, for example, the condition being treated, the route of administration, the severity of the condition being treated, and the condition and prior medical history of the patient being treated. However, it is within the skill of the art to start doses of the compound at levels lower than required to achieve the desired therapeutic effect and to gradually increase the dosage until the desired effect is achieved. It will be understood, however, that the specific dose level for any particular patient can depend upon a variety of factors including the genetic makeup, body weight, general health, diet, time and route of administration, combination with other drugs and the particular condition being treated, and its severity. For the treatment of insomnia, preferably one dose is administered prior to bedtime.

As mentioned above, in some embodiments the preferable dosage can be between about 0.001 milligrams and about 350 milligrams. In some aspects, the dosage can be about 50 milligrams to about 350 milligrams. More preferably, the dosage can be between about 75 milligrams and 300 milligrams. Also, in some aspects, the dosage can be between about 0.1 milligrams and 20 milligrams or between about 0.5 milligrams and 10 milligrams. The dosage also can be between about 1 milligram and about 6 milligrams. Preferably, the dosage can be about 0.5 milligrams, 1 milligram, about 2 milligrams, about 3 milligrams, about 4 milligrams, about 5 milligrams or about 6 milligrams. Further, the dosage can be about 7 milligrams, about 8 milligrams, about 9 milligrams, or about 10 milligrams. The lower dosage ranges are particularly desirable for sleep-related indications, while the higher dosage ranges are particularly desirable for depression and anxiety-related indications.

EXAMPLES

Example 1

Assessment of the Effect of Food on the Pharmacokinetics of Doxepin

A study assessed the effect of food on the pharmacokinetics (PK) of doxepin in healthy subjects. It was a single-center, phase 1, randomized, open-label, single dose, two-way crossover study conducted in sixteen healthy, young adult male and female subjects. Screening procedures were performed within 14 days prior to enrollment.

Following screening procedures and baseline assessments, eligible subjects were randomly assigned to one of two treatment sequences (fed-fasted or fasted-fed). Subjects received a single 6 milligram dose of doxepin in the morning under either fed or fasted conditions on 2 dosing days (Day 1 and Day 8). There were approximately 7 days between each dose. Enrolled subjects were admitted to the study center on the evening before study drug dosing (Day 0 and Day 7) and remained at the study center for approximately 5 days. All subjects were dosed under both fed and fasted conditions during the study as illustrated in FIG. 1.

Subjects being dosed under fasted conditions were required to fast overnight for at least 10 hours prior to study drug administration and for 4 hours after study drug administration. Fluids were restricted from 1 hour predose to 1 hour postdose, except for water taken at the time of dosing. Subjects being dosed under fed conditions were dosed approximately 5 minutes after eating a high-fat, high-calorie standardized breakfast (to be ingested within 25 minutes). Subjects were required to ingest the entire contents of the breakfast. All subjects were required to remain in bed for approximately 4 hours after dosing.

Contents of the high-fat, high-calorie standardized breakfast were:

Two eggs fried in butter;

Two slices of bacon;

240 mL (8 fl. oz) whole milk;

57 g (2 oz) of hash browned potatoes; and

Two slices of toasted white bread with butter.

The total amount of protein, fat, and carbohydrate that made up this meal was approximately 33, 55, and 58 g, respectively. The total calorie content was approximately 850 kcal.

Subjects were dosed on Day 1 and Day 8. The PK profiles were evaluated on Days 1 through 5 and Days 8 through 12. Blood samples were collected at predose (0 hour) and at 0.08, 0.17, 0.25, 0.5, 0.75, 1, 1.5, 2, 3, 4, 6, 8, 12, 24, 36, 48, 60, 72, and 96 hours postdose. The samples were analyzed for doxepin and doxepin metabolite concentrations in plasma. Plasma concentrations of doxepin were measured using validated high performance liquid chromatography coupled to tandem mass spectrometry. The lower limit of quantification for doxepin was 0.05 ng/mL. The following PK parameters were estimated by noncompartmental methods using actual elapsed time from dosing:

| | |
|---|---|
| $C_{max}$ (ng/mL) | Maximum observed plasma concentration, obtained directly from the observed concentration versus time data. |
| $T_{max}$ (h) | Time to maximum plasma concentration, obtained directly from the observed concentration versus time data. |
| $AUC_{0-\infty}$ (ng · h/mL) | Area under the curve from time zero extrapolated to infinity, calculated by linear up/log down trapezoidal summation and extrapolated to infinity by addition of the last quantifiable concentration divided by the elimination rate constant ($AUC_{0-Tlast} + C_{last}/\lambda_z$). If the extrapolated area ($C_{last}/\lambda_z$) was greater than 30% of $AUC_{0-\infty}$, then $AUC_{0-\infty}$ was set to missing. |
| $AUC_{0-Tlast}$ (ng · h/mL) | Area under the curve from time zero to time of last measurable concentration, calculated by linear up/log down trapezoidal summation. |
| $AUC_{0-24}$ (ng · h/mL) | Area under the curve from time zero until 24 hours, calculated by linear up/log down trapezoidal summation. If the 24 h sample was missing or below the lower limit of quantification, $AUC_{0-Tlast}$ was to be reported as $AUC_{0-24}$. |
| $AUC_{0-48}$ (ng · h/mL) | Area under the curve from time zero until 48 hours, calculated by linear up/log down trapezoidal summation. If the 48 h sample was missing or below the lower limit of quantification, $AUC_{0-Tlast}$ was to be reported as $AUC_{0-48}$. |
| $AUC_{0-72}$ (ng · h/mL) | Area under the curve from time zero until 72 hours, calculated by linear up/log down trapezoidal summation. If the 72 h sample was missing or below the lower limit of quantification, $AUC_{0-Tlast}$ was to be reported as $AUC_{0-72}$. |
| $AUC_{0-96}$ (ng · h/mL) | Area under the curve from time zero until 96 hours, calculated by linear up/log down trapezoidal summation. If the 96 h sample was missing or below the lower limit of quantification, $AUC_{0-Tlast}$ was to be reported as $AUC_{0-96}$. |
| $\lambda_z$ (1/h) | Elimination rate constant associated with the terminal (log-linear) portion of the curve. This was estimated via linear regression of time versus log concentration. Visual assessment was used to identify the terminal linear phase of the concentration-time profile. A minimum of three data points were used for determination. |
| $t_{1/2}$ (h) | Apparent terminal half-life, determined as $\ln 2/\lambda_z$. |
| CL/F (L/h) | Apparent oral clearance, calculated as dose divided by $AUC_{0-\infty}$. |
| Vd/F (L) | Apparent volume of distribution, calculated as $(CL/F)/\lambda_z$. |

Concentration-Time Profiles

With reference to Table 1, following a single 6 milligram dose administration of doxepin in fasted state (Treatment A) and fed state (Treatment B), mean plasma concentrations of doxepin increased, reaching $C_{max}$ at 3.0 and 6.0 hours postdose, respectively. Doxepin plasma concentrations, reached mean $C_{max}$ values of 0.854 and 0.951 ng/mL in fasted and fed states, respectively. For both treatments, plasma doxepin concentrations declined thereafter and remained quantifiable up to 48 hours postdose (the lower limit of quantification was 0.05 ng/mL). Detectable plasma levels of doxepin were first observed at 30 minutes postdose in both the fed and fasted states (six and five subjects, respectively). All subjects had detectable concentrations of doxepin by 90 minutes postdose. Median $T_{max}$ was delayed by approximately 3.0 hours in the fed state (6.0 hours) as compared to the fasted state (3.0 hours). However, the range of values was similar for both treatments. Mean $t_{1/2}$ values were comparable for fed and fasted states (16.5 versus 14.4 hours, respectively).

The effect of a high-fat meal on the pharmacokinetics of the 6 milligram doxepin tablet was assessed and statistical comparisons of doxepin pharmacokinetic parameters between treatments are presented in Table 3.

The 90% confidence intervals for the ratio of population geometric least-square means between fed and fasted treatments was not completely contained within the equivalence limits of 80-125% for $C_{max}$, and were outside the equivalence limits for $AUC_{0-\infty}$ and $AUC_{0-Tlast}$, indicating that there was a food effect on exposure. Under fed conditions, $AUC_{0-\infty}$, $AUC_{0-Tlast}$, and $C_{max}$ were higher by 41%, 46%, and 15%, respectively, compared to fasted conditions.

TABLE 3

Statistical Comparison of Doxepin Pharmacokinetic Parameters Between Treatments

| Parameter (unit) | Treatment [a] | N | Geometric LS Mean | Pairwise Comparisons Pair | Ratio (%) | 90% CI |
|---|---|---|---|---|---|---|
| $AUC_{0-\infty}$ (ng · h/mL) | Fed | 16 | 15.14 | Fed/Fasted | 141.3 | (124.7, 160.1) |
|  | Fasted | 15 | 10.72 |  |  |  |
| $AUC_{0-Tlast}$ (ng · h/mL) | Fed | 16 | 13.39 | Fed/Fasted | 145.6 | (127.0, 166.9) |
|  | Fasted | 15 | 9.194 |  |  |  |
| $C_{max}$ (ng/mL) | Fed | 16 | 0.822 | Fed/Fasted | 114.6 | (101.8, 129.1) |
|  | Fasted | 15 | 0.717 |  |  |  |

Note:
Results are based on mixed effect analysis of variance with sequence, period and treatment as fixed effects and subject within sequence as a random effect.
[a] 6 milligram doxepin tablet, under fed or fasted conditions.

TABLE 1

Summary Statistics [arithmetic mean (CV %)] of Plasma Doxepin Pharmacokinetic Parameters

|  | Treatment [a] | |
|---|---|---|
| Parameter (unit) | Fed (N = 16) | Fasted (N = 15) |
| $C_{max}$ (ng/mL) | 0.951 (58.8) | 0.854 (63.2) |
| $T_{max}$ (h) [b] | 6.0 (2.0-6.0) | 3.0 (1.5-6.0) |
| $AUC_{0-\infty}$ (ng · h/mL) | 18.6 (70.2) | 14.1 (80.6) |
| $AUC_{0-Tlast}$ (ng · h/mL) | 16.8 (74.0) | 12.6 (85.7) |
| $t_{1/2}$ (h) | 16.5 (23.8) | 14.4 (42.2) |
| $\lambda_z$ (1/h) | 0.0445 (26.6) | 0.0623 (65.9) |

[a] 6 milligram doxepin tablet, under fed or fasted conditions.
[b] Indicates median (range) values.

Table 2 shows the estimates of clearance and volume of distribution for doxepin. Mean CL/F and Vd/F were 43% and 14% lower in the fed state compared to the fasted state, respectively. Mean CL/F values were lower in the fed (477 L/h) versus the fasted (837 L/h) states. Mean Vd/F remained almost unchanged for fed (10280 L) and fasted (11930 L) states.

TABLE 2

Summary Statistics [arithmetic mean (CV %)] of Mean Clearance and Volume of Distribution for Doxepin

|  | Treatment [a] | |
|---|---|---|
| Parameter (unit) | Fed (N = 16) | Fasted (N = 15) |
| CL/F (L/h) | 477 (63.4) | 837 (114.3) |
| Vd/F (L) | 10280 (43.3) | 11930 (46.9) |

[a] 6 milligram doxepin tablet, under fed or fasted conditions.

Conclusions

Following a single 6 milligram dose of doxepin, a food effect was observed on the pharmacokinetics of doxepin. In the fed state, the maximum concentration ($C_{max}$) and exposure ($AUC_{0-\infty}$) of doxepin were approximately 15% and 41% higher, respectively, compared to the fasted state, and median $T_{max}$ was delayed by approximately 3.0 hours. The increase in exposure was statistically significant and represents an increase in bioavailability in the fed state (Table 4).

TABLE 4

| Parameter | Arithmetic Mean (Fed condition) | Arithmetic Mean (Fasted condition) | Effect of Food (% of fasted state)[a] |
|---|---|---|---|
| $AUC_{0-\infty}$ (ng · h/mL) | 18.6 | 14.1 | 141 |
| $C_{max}$ (ng/mL) | 0.951 | 0.854 | 115 |
| $T_{max}$ (h)[b] | 6 | 3 | 200 |

[a]Note that percentages documenting food effect on $C_{max}$ and AUC are calculated from geometric LS means rather than the arithmetic means presented in this table
[b]$T_{max}$ is presented as a median value Many modifications and variations of the embodiments described herein may be made without departing from the scope, as is apparent to those skilled in the art. The specific embodiments described herein are offered by way of example only.

We claim:

1. A method of treating insomnia in a patient in need thereof, the method comprising:
administering between about 0.5 mg and about 7 mg doxepin to the patient, wherein the doxepin is administered at least 3 hours after consuming a meal to provide faster onset of action and minimize potential for next day sedation effects.

2. The method of claim 1, wherein the doxepin is administered in an amount of about 3 milligrams.

3. The method of claim 1 wherein the doxepin is administered in an amount of about 6 milligrams.

4. The method of claim 1 wherein the doxepin is administered as a tablet, capsule or liquid.

5. The method of claim 1, wherein the doxepin is administered as a unit dosage form.

6. The method of claim 1, wherein the doxepin is administered as an oral dosage form.

7. The method of claim 1, wherein the doxepin helps the patient fall asleep.

8. The method of claim 1, wherein the doxepin helps the patient stay asleep.

9. The method of claim 1, wherein administration of doxepin to a group of patients after a high fat meal provides an increase in area under the curve (AUC) compared to administration of doxepin to a group of fasted patients.

10. The method of claim 9, wherein the increase in AUC is about 41%.

11. The method of claim 1, wherein administration of doxepin to a group of patients after a high fat meal provides an increase in maximum plasma concentration ($C_{max}$) compared to administration of doxepin to a group of fasted patients.

12. The method of claim 11, wherein the increase in $C_{max}$ is about 15%.

13. The method of claim 1, wherein the doxepin is administered within about one hour of bedtime.

14. The method of claim 1, wherein the doxepin is administered as doxepin hydrochloride.

15. A method of treating insomnia in a patient in need thereof, the method comprising:
   administering between about 0.5 mg and about 7 mg doxepin to the patient, wherein the doxepin is administered at least 3 hours after consuming a meal, wherein administration of doxepin to a group of patients after a high fat meal compared to administration of doxepin to a group of fasted patients provides:
   an increase in area under the curve (AUC) of doxepin;
   an increase in maximum plasma concentration ($C_{max}$) of doxepin; or
   a delay in median time to reach maximum plasma concentration ($T_{max}$) of doxepin.

16. The method of claim 15, wherein the increase in AUC is about 41%.

17. The method of claim 15, wherein the increase in $C_{max}$ is about 15%.

18. The method of claim 15, wherein the delay in $T_{max}$ is about 3 hours.

19. The method of claim 15, wherein administration of doxepin to a group of patients after a high fat meal compared to administration of doxepin to a group of fasted patients provides:
   an increase in AUC of about 41%;
   an increase in $C_{max}$ of about 15%; and
   a delay in $T_{max}$ of about 3 hours.

* * * * *